United States Patent [19]

Larson et al.

[11] Patent Number: 5,667,842

[45] Date of Patent: Sep. 16, 1997

[54] ABRASIVE ARTICLES INCORPORATING ADDITION POLYMERIZABLE RESINS AND REACTIVE DILUENTS, AND METHODS OF MAKING SAID ABRASIVE ARTICLES

[75] Inventors: Eric G. Larson, Lake Elmo; Ernest L. Thurber, St. Paul; Alan R. Kirk, Cottage Grove; Gregg D. Dahlke, St. Paul; Elizabeth C. Edblom, Minneapolis, all of Minn.; Don H. Kincaid, Hudson, Wis.

[73] Assignee: Minnesota Mining and Manufacturing Company, St. Paul, Minn.

[21] Appl. No.: 474,289

[22] Filed: Jun. 7, 1995

Related U.S. Application Data

[62] Division of Ser. No. 144,199, Dec. 20, 1993, abandoned, which is a division of Ser. No. 334,817, Nov. 4, 1994, Pat. No. 5,523,152, which is a continuation-in-part of Ser. No. 143,824, Oct. 27, 1993, abandoned.

[51] Int. Cl.$^6$ .................... B05D 1/38; B24D 3/00; C09K 3/14
[52] U.S. Cl. ............. 427/258; 427/261; 427/407.1; 51/295; 51/298; 51/307; 442/73
[58] Field of Search ............. 51/298, 307; 428/245, 428/290; 427/258, 261, 267, 407.1

[56] References Cited

U.S. PATENT DOCUMENTS

| | | | |
|---|---|---|---|
| 2,882,262 | 4/1959 | Smith et al. | 526/264 |
| 4,179,478 | 12/1979 | Rosenkranz et al. | 525/113 |
| 4,180,474 | 12/1979 | Schuster et al. | 525/451 |
| 4,382,135 | 5/1983 | Sinka et al. | 526/301 |
| 4,588,419 | 5/1986 | Caul et al. | 51/295 |
| 4,591,651 | 5/1986 | Delmas et al. | 549/473 |
| 4,903,440 | 2/1990 | Larson et al. | 51/298 |
| 5,047,259 | 9/1991 | Oberkobusch et al. | 427/474 |
| 5,047,261 | 9/1991 | Moussa et al. | 427/27 |
| 5,055,113 | 10/1991 | Larson et al. | 51/298 |
| 5,178,646 | 1/1993 | Barber, Jr. et al. | 51/298 |
| 5,192,815 | 3/1993 | Okada et al. | 523/115 |
| 5,236,472 | 8/1993 | Kirk et al. | 51/298 |

FOREIGN PATENT DOCUMENTS

| | | |
|---|---|---|
| 0 222 059 | 5/1987 | European Pat. Off. . |
| 0 400 658 | 5/1990 | European Pat. Off. . |
| 0 400 785 | 12/1990 | European Pat. Off. . |
| 49-133491 | 12/1974 | Japan . |
| 59-171948 | 9/1984 | Japan . |
| 1245-569 | 9/1988 | Japan . |
| 02000603 A2 | 1/1990 | Japan . |
| 4 308 578 | 10/1992 | Japan . |
| 930668 | 7/1963 | United Kingdom . |
| WO88/09783 | 12/1988 | WIPO . |

OTHER PUBLICATIONS

July 1993, Amer. Chem. Soc. Search for 2–Propenoic acid, phosphinylidynetris(oxy-2,1–3ethanediyl) ester.
Jul. 1993, Amer. Chem. Soc. Search for N–(Acryloyl)morpholine.
Jul. 1993, Amer. Chem. Soc. Search for 2–Propenoic acid, (methylimino)di–2,1–ethanediyl ester.
Jul. 1993, Amer. Chem. Soc. Search for 2–Propenoic acid, carbonylbis(imino-2,1–ethanediyl) ester.
1992, Amer. Chem. Soc. Search for 2–(Acryloyloxyethyl)pyridine.
1992, Amer. Chem. Soc. Search for N–(Acryloyloxyethyl) tetrahydrophthalimide.
1992 Amer. Chem. Soc. Search for 2–Acryloyloxymethyl) furan.

(List continued on next page.)

*Primary Examiner*—Tae Yoon
*Attorney, Agent, or Firm*—Gary L. Griswold; Walter N. Kirn; Doreen S. L. Gwin

[57] ABSTRACT

Abrasive articles made using a coatable, addition polymerizable binder precursor composition are described, as well as methods of making same. The compositions comprise a reactive diluent compound and preferably an addition polymerizable resin, the reactive diluent being an organic compound selected to be especially effective in solubilizing aminoplast resins.

15 Claims, 5 Drawing Sheets

OTHER PUBLICATIONS

1992, Amer. Chem. Soc. Search for (Diacryloyloxyethyl) isophthalate.

1992 Amer. Chem. Soc. Search for N–(Acryloyloxyethyl)phthalimide.

Jul. 1993, Amer. Chem. Soc. Search for 3–(Acryloyloxyethyl)2–oxazolidinone.

1992 Amer. Chem. Soc. Search for N–(Acryloyloxyethyl) hexahydropthalimide.

1992 Amer. Chem. Soc. Search for (Diacryloyloxyethyl) phthalate (DAP).

Chemical Abstracts, 170610x Imido(meth)acrylates and Resin Compositions and Solder Resists Containing Them, 76–Electric Phenomena, vol. 112, 1990 pp. 847–848.

Derwent Publications Ltd., 89–327660/45 (1989).

Chemical Abstracts, 7996b Resin Compositions and Heat–Resistant Coatings for Optical Fibers, 42–Coatings, vol. 116, 1992.

Derwent Publications Ltd., 91–129156/18 (1991).

Chemical Abstracts, 3378s Phthalimide Derivatives, 27–Heterocycles, vol. 80, 1974, p. 295.

Derwent Publications Ltd., JA–087768 (1973).

Sartomer Product Catalog, 1992, Sartomer Company, Inc.

Material Safety Data Sheet for "Photomer 6173", Diamond Shamrock Chemicals Company, 1981.

Photomer Radiation Curing Chemicals Product Description Listing, Jan. 1993.

Chemical Abstracts, 172726a Crosslink–hardenable Resin Compositions, 42–Coatings, vol. 82, 1975, p. 99.

Derwent Publications Ltd., 20159W/12 (1973).

Chemical Abstracts, 140208j Acryloyloxyalkyl Benzoate–acrylate Copolymers as Ultraviolet Light Absorbers and a Method for Their Preparation, 62–Essential Oils, Cosmetics, vol. 111, 1989, p. 381.

Derwent Publications, Inc., 88–368605/51 (1987).

English Language Abstract of "Photopolymerisation De Monomers Multifonctionnels", Eur. Polym. J. vol. 27, No. 4/5, p. 411 (1991).

STN International Registry File Search Statistics, 24 Nov. 1992, pp. 1–55.

D'Alelio et al., Journal of Polymer Science: Part A–1, vol. 5, (1967) pp. 287–321.

Photopolymerization of Multifunctional Monomers, Decker and Moussa—English Translation of full article provided.

Henry Feuer and Una E. Lynch, *Synthesis and Reaction of Unsaturated N–Metholamides*, "The Synthesis and Reactions of Unsaturated N–Methylolamides," Oct. 20, 1953, vol. 75, pp. 5027–5029.

Chemical Abstracts 93:96890j Photochemical hardening of oligoester maleate compositions in an air medium, by Rot. A.S.; Chernyakov, E. A.; Gerber, V.D. (L'vov. Lesotekh, Inst., Lvov, USSR) Lakokras, Mater, Ikh Primen. 1980, (3), 27–9 (Russ).

Derwent Publication Ltd., London, GB; AN 91–345126 C47?—Abstract of SU A, 1 634 465 (Spetstekhnosnastka), Mar. 15 1991.

ABRASIVE ARTICLES INCORPORATING ADDITION POLYMERIZABLE RESINS AND REACTIVE DILUENTS, AND METHODS OF MAKING SAID ABRASIVE ARTICLES

This is a division of application Ser. No. 08/144,199 filed Dec. 20, 1993, abandoned, which is a division of application Ser. No. 08/334,817 filed on Nov. 4, 1994, which is now U.S. Pat. No. 5,523,152 which is CIP of application Ser. No. 08/143,824 filed on Oct. 27, 1993, abandoned.

BACKGROUND OF THE INVENTION

1. Field of the Invention

This invention relates to abrasive articles utilizing a binder which secures abrasive grains to a backing sheet, on fibers of a fibrous mat, or in a shaped mass, and to methods of making such articles utilizing a binder precursor that includes a reactive diluent.

2. Description of the Related Art

Coated abrasives generally comprise a flexible backing upon which a binder holds and supports a coating of abrasive grains. Coated abrasives typically employ a "make" coating comprising a resinous binder material. The make coating secures the abrasive grains to the backing. A "size" coating of resinous binder material applied over the make coating and abrasive grains firmly bonds the abrasive grains to the backing. Additionally, the abrasive grains are generally oriented with their longest dimension perpendicular to the backing to provide an optimum cut rate.

In a typical manufacturing process for making coated abrasives using thermally curable condensation binder precursors (for example resole phenolic resins), the make coating is formed from such a precursor composition, which is first applied to the backing. This is followed by electrostatic projection of abrasive grains into the make coating precursor. The make coating precursor is then partially thermally cured in order to set the abrasive grains. Next, a thermally curable condensation size coating precursor (which may be the same or different than the make coating precursor) is applied over the abrasive grains and make coating. Finally, the coating precursors are fully thermally cured.

U.S. Pat. No. 5,178,646 (Barber et al.) discloses thermally curable abrasive binder precursors containing reactive diluents. The thermally curable abrasive binder precursor containing reactive diluents may be blended with up to 50% by weight of an ethylenically unsaturated-monomer.

Non-woven abrasive articles typically comprise a fibrous web of synthetic and/or natural fibers which have on at least a portion of their surface an abrasive coating comprising abrasive grains and a binder which binds the fibers together. Binders and reactive diluents mentioned in the Barber et al. patent may be employed in the production of nonwoven abrasives.

In recent years radiation energy curable resins have been proposed as binders for coated abrasives as a substitute for conventional thermally curable condensation resins. Radiation energy curable resins can be cured much more rapidly than can thermally curable condensation resins. If additional heat is provided in an attempt to more rapidly cure phenolic resins, the viscosity of the phenolic resin will decrease, thereby resulting in loss of mineral orientation when used in make coatings.

The resinous adhesives used for abrasives production are preferably tailored such that they have cured properties desired for use as an abrasive article binder for each application. For example, in the coarse grade applications (larger particle sizes), the cured resinous adhesive(s) are most preferably hard, heat resistant and tough. Alternatively, in the fine grade applications (smaller particle sizes), the cured resinous adhesive(s) should be flexible and less hard.

One example of a typical resinous adhesive is a radiation curable aminoplast resin. The aminoplast resins have at least one pendant unsaturated group per molecule or oligomer. These unsaturated groups are preferably positioned $\alpha,\beta$ with respect to the carbonyl moiety, and can be acrylate, methacrylate or acrylamide type groups. Examples of such materials include N-(hydroxymethyl)acrylamide, N,N'-oxydimethylenebisacrylamide, ortho and para acrylamidomethylated phenol, acrylamidomethylated phenolic novolak and combinations thereof. These materials are further described in U.S. Pat. Nos. 4,903,440, 5,055,113 and 5,236,472.

U.S. Pat. No. 4,588,419 (Caul et al.) describes radiation-curable coated abrasive material constructions in which acrylated epoxy and acrylated urethane resins are diluted with a number of monofunctional and polyfunctional acrylates as reactive diluents, including hexanediol diacrylate and trimethylolpropane triacrylate, as well as N-vinyl-2-pyrrolidone. The disclosed diluents, however, are not aromatic or polycyclic, and the acrylates are not effective solvents for aminoplast resins, and may not produce hard resins as preferred in the present application.

U.S. Pat. No. 4,927,431 (Buchanan, et al.) describes a resin binder for abrasive articles comprised of a blend of resole phenolic resin with a radiation-curable component containing pendant acrylate groups. The primary attribute of these cured blends is a hardness closer to that of phenolic resins and substantially higher than acrylate binders.

Thus, there is a need for reactive diluents which exhibit excellent solubility for acrylamide resins, which are highly reactive to both photochemical and thermal free-radical polymerization (defined as "addition polymerizable" herein), which exhibit low vapor pressures, which exhibit low viscosity at temperatures about 20° C. and which enhance or, at the least, do not diminish the hardness of resins in which they are used. Copending U.S. application Ser. No 08/334,817 filed Nov. 4, 1994, now U.S. Pat. No. 5,523,152 which is a continuation-in-part application of U.S. application Ser. No. 08/143,824 filed Oct. 27, 1993, now abandoned, discloses such reactive diluents.

SUMMARY OF THE INVENTION

The present invention overcomes or reduces many of the aforementioned problems associated with previously known coatable, addition polymerizable binder precursor compositions as they are used to make abrasive articles.

In accordance with the first aspect of the present invention, abrasive articles are presented comprising a plurality of abrasive grains dispersed and adhered within a binder, the binder formed from a coatable, addition polymerizable binder precursor composition comprising:

(i) an optional addition polymerizable resin which, if present, is preferably free radically polymerizable, more preferably an aminoplast resin having $\alpha,\beta$-unsaturated carbonyl groups; and (ii) a reactive diluent, wherein the reactive diluent is an organic compound selected from the group consisting of:

(a) compounds selected from the group consisting of compounds within general formula (I):

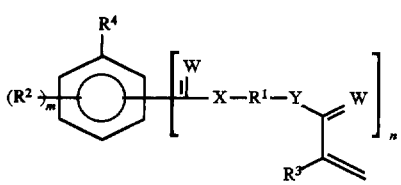

(I)

wherein:

R¹ is an organic radical devoid of reactive groups other than optional ethylenically-unsaturated groups and is selected from the group consisting of radicals having from 1 to 12 carbon atoms;

R² is selected from the group consisting of: i) organic radicals devoid of reactive groups other than optional ethylenically-unsaturated groups and selected from the group consisting of organic radicals having from 1 to 12 carbon atoms, and ii) moieties which do not substantially terminate polymerization of ethylenically-unsaturated groups;

R³ is selected from the group consisting of —H and organic radicals devoid of reactive groups other than optional ethylenically-unsaturated groups and selected from the group consisting of organic radicals having from 1 to 12 carbon atoms;

R⁴ is selected from the group consisting of —H, —OH, —O—C(=O)—C(R³)=CH₂, and —NR³—C(=O)—C(R³)=CH₂;

W, X and Y are independently selected from the group consisting of O, S, NR³;

m is an integer ranging from 0 to 2, with the proviso that when m=2, R²=adjacent substitutions which together form fused organic ring structures, preferably selected from the group consisting of fused aromatic, fused cycloaliphatic, fused bicycloaromatic, and fused heterocyclic rings; and n is either 1 or 2;

(b) aromatic compounds selected from the group consisting of compounds within general formula (II):

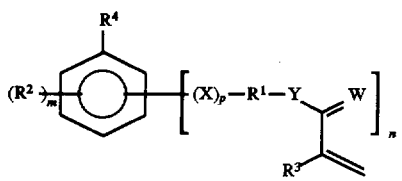

(II)

wherein:

R¹, R², R³, R⁴, W, X, Y, m and n are as defined for general formula (I) and p is 0 or 1, with the proviso that when R¹ is —CH₂CH₂—, R⁴ is H, and m is O, then X, Y, and W cannot all be O, and with the proviso that when p is O and R¹ is —CH₂—, Y cannot be NR₃ or O;

(c) N-substituted succinimide derivatives selected from the group consisting of compounds within general formula (III):

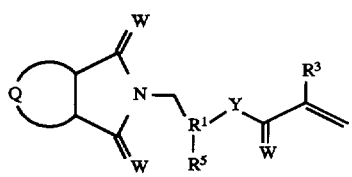

(III)

wherein:

R¹, R³, W and Y are as defined for general formula (I);

R⁵ is selected from the group consisting of —H, —(R¹)ₜ —Y—C(=W)—CR₃=CH₂, and C₁-C₁₂ (inclusive) organic radicals;

Q is selected from the group consisting of cycloaliphatic residues (preferably having from 3 to about 10 carbon atoms), bicycloaliphatic residues (preferably having from 3 to about 20 carbon atoms), and aromatic residues, wherein the residues may have optional ring substituents which do not substantially interfere with free radical polymerization of ethylenically unsaturated groups; and t is 0 or 1;

(d) heterocyclic compounds selected from the group consisting of compounds within general formula (IV):

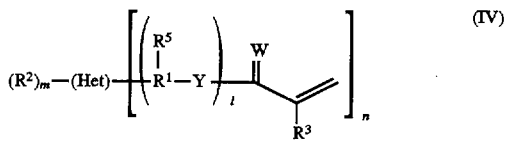

(IV)

wherein:

R¹, R², R³, W, Y, m and n have the meaning set forth for general formula (I);

R⁵ is selected from the group consisting of —H, —(R¹)ₜ —Y—C(=W)—CR₃=CH₂, and C₁-C₁₂ (inclusive) organic radicals;

(Het) is a cyclic organic radical having at least one ring heteroatom;

l is 0 or 1; and t is 0 or 1; and (e) heterocyclic compounds selected from the group consisting of compounds within general formula (V):

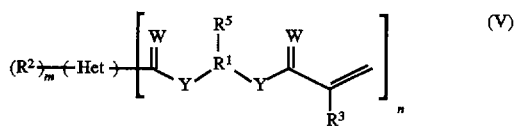

(V)

wherein:

R¹, R², R³, R⁵, W, Y, m and n have the meanings set forth for general formula (IV);

and mixtures thereof.

In general formulas (I)–(V), R¹ is preferably selected from —CₓH₂ₓ— and —CᵧH₂ᵧ—O—Cᵧ'H₂ᵧ'— wherein x is an integer ranging from 1 to 12 (inclusive) and y and y' are independently selected from integers ranging from 1 to 6 (inclusive).

The term "addition polymerizable resin" as used herein means a composition including one or more ethylenically-unsaturated monomers or oligomers such as aminoplasts having at least one pendant ethylenically unsaturated group, triethylene glycol diacrylate, acrylated epoxies, acrylated urethanes, and the like.

The term "thermally curable condensation resins" as used herein means resins which are primarily curable by thermal means, for example phenolic resins, urea-aldehyde resins, and the like. It is understood by those skilled in the art that "addition polymerizable resins", although primarily cured by radiation energy, may also be cured (or their cure accelerated by) heating. As used herein, the term "coatable, addition polymerizable binder precursor composition" means a coatable, homogeneous mixture including uncured addition polymerizable resin, reactive diluent, and optionally a non-reactive diluent, which, upon curing, becomes a binder. (The term does not exclude thermally curable condensation resin precursors, although exclusion of the latter may be particularly preferred.) The term "binder" means a cured binder precursor composition.

The term "coatable", as used herein, means that the binder precursor compositions of the invention may be easily coated or molded onto a substrate using any of one or more coating devices which are conventional in the abrasives art, such as knife coaters, roll coaters, flow-bar coaters, and the like. This characteristic may also be expressed in terms of viscosity of the compositions. The viscosity of the inventive coatable, radiation curable binder precursor compositions should not exceed about 2000 centipoise (cps), measured using a Brookfield viscometer, no. 2 spindle, 60 rpm, at 25° C.

The term "reactive" when used in the context "reactive diluent" means that the compound has moieties allowing it to be polymerized with the other resin components, for example, acrylate moieties.

The term "diluent" is used in the sense that the reactive diluent compounds (and optional inert diluent liquids) dilute the concentration of radiation curable resin in the binder precursor compositions useful in the invention, and does not mean that the compositions are necessarily decreased in viscosity, although viscosity reduction is preferred.

The term "polar" as used herein has its generally accepted meaning and means that the functional group exhibits an increased electronegativity relative to surrounding atoms, and, in particular, relative to adjacent carbon atoms. A polar group preferably includes one or more heteroatoms such as N (nitrogen) and O (oxygen).

Another aspect of the invention is a coated abrasive article comprising a backing upon which an abrasive coating comprising a plurality of abrasive grains and a binder is attached, at least a portion of the binder formed from a coatable, addition polymerizable binder precursor composition as previously described in reference to the first aspect of the invention.

A third aspect of the invention is a coated abrasive article comprising a backing, a make coating on at least one major surface of the backing, a plurality of abrasive particles adhered to the backing by means of the make coating, and a size coating over the abrasive grains and make coating, and an optional supersize coating over the size coating, wherein at least one of the make, size, or supersize coatings is formed from a coatable, addition polymerizable binder precursor composition as above described in reference to the previous aspects of the invention.

A fourth aspect of the invention is a coated abrasive article comprising a backing and an abrasive coating, wherein the backing has at least one of a saturant coating, a presize coating, or a backsize coating, wherein at least one of the saturant, presize, or backsize coatings is formed from a coatable, addition polymerizable binder precursor composition as above described in reference to the previous aspects of the invention.

Another aspect of the invention is a nonwoven article of the type comprising a lofty, open, fibrous mat of fibers, at least some of which are bonded together at points where they contact with a binder, wherein the binder is derived from the coatable, addition polymerizable binder precursor composition described in the previous aspects of the invention. Nonwoven articles within the invention optionally have a plurality of abrasive grains adhered to the fibers by the binder.

Still another aspect of the invention is a method of making the inventive nonwoven articles. The method includes the steps of:

(a) coating at least a portion of the fibers of a lofty, open fibrous mat with a coatable, addition polymerizable binder precursor composition to form a coated mat, the composition being the inventive composition as above described; and (b) exposing the coated mat to conditions sufficient to cure the binder precursor composition.

One particularly preferred method comprises:

(a) combining an addition polymerizable resin with a reactive diluent compound to form a coatable, addition polymerizable binder precursor composition, at a temperature below that necessary to cure the coatable, addition polymerizable binder precursor composition;

(b) combining abrasive particles with the coatable, addition polymerizable binder precursor composition to form an abrasive filled coatable, addition polymerizable binder precursor composition;

(c) coating the abrasive-filled, coatable, addition polymerizable binder precursor composition onto at least a portion of the fibers of a lofty, open fibrous mat to form a coated mat of fibers; and (d) exposing the coated mat of step (c) to conditions sufficient to cure the coatable, addition polymerizable binder precursor composition, wherein the reactive diluent compound is as previously defined in the first aspect of the invention.

An optional step is to apply additional abrasive grains to the coated mat produced by step (c) prior to step (d).

A further method is presented for making a coated abrasive article, the method including the steps of:

(a) coating a backing with a slurry comprising the above-described coatable, addition polymerizable binder precursor composition comprising a compound within general formulas (I)–(V), abrasive grains, and an optional addition polymerizable resin to provide a slurry-coated backing; and (b) subjecting the slurry to conditions sufficient to cure the coatable, addition polymerizable binder precursor composition.

A preferred method of making a coated abrasive article includes the steps of:

(a) applying a first coatable, addition polymerizable binder precursor composition to at least one major surface of a backing to form a make coating precursor, the coatable addition polymerizable binder precursor composition comprising a reactive diluent and an optional addition polymerizable resin having the compositions as above described;

(b) applying abrasive grains to the make coating precursor of step (a) to form a wet abrasive coating;

(c) subjecting the wet abrasive coating to conditions sufficient to at least partially solidify the make coating precursor to form a first intermediate structure;

(d) applying a second coatable, addition polymerizable binder precursor composition optionally including a compound as defined in claim 1 to the first intermediate structure to form a second intermediate structure having a size coating; and (e) subjecting the second intermediate structure to conditions sufficient to cure the first and second coatable, addition polymerizable binder precursor compositions.

The optional addition polymerizable resin is preferably a radiation-curable aminoplast resin as described in U.S. Pat. Nos. 4,903,440, 5,055,113, and 5,236,472. Preferred formulations of radiation energy curable aminoplasts with one or more radiation energy curable reactive diluents described in general formula (I) provides coatable, low viscosity, non-volatile, and rapid curing binder systems that cure to substantial hardness.

Optionally, the coatable, addition polymerizable binder precursor compositions may include up to about 150 weight percent (of the total weight of the addition polymerizable resin precursors) of thermally curable condensation monomers and oligomers. Thus, conventional thermally curable condensation resins such as phenol-formaldehyde, urea-formaldehyde, melamine, and furfural (as well as reactive diluents for such resin precursors as disclosed in the above mentioned Barber et al. patent) may be admixed with the addition polymerizable binder precursors.

Further aspects and advantages of the invention will become apparent from the description of preferred embodiments which follows.

DESCRIPTION OF PREFERRED EMBODIMENTS

Reactive Diluents

Figure 1:
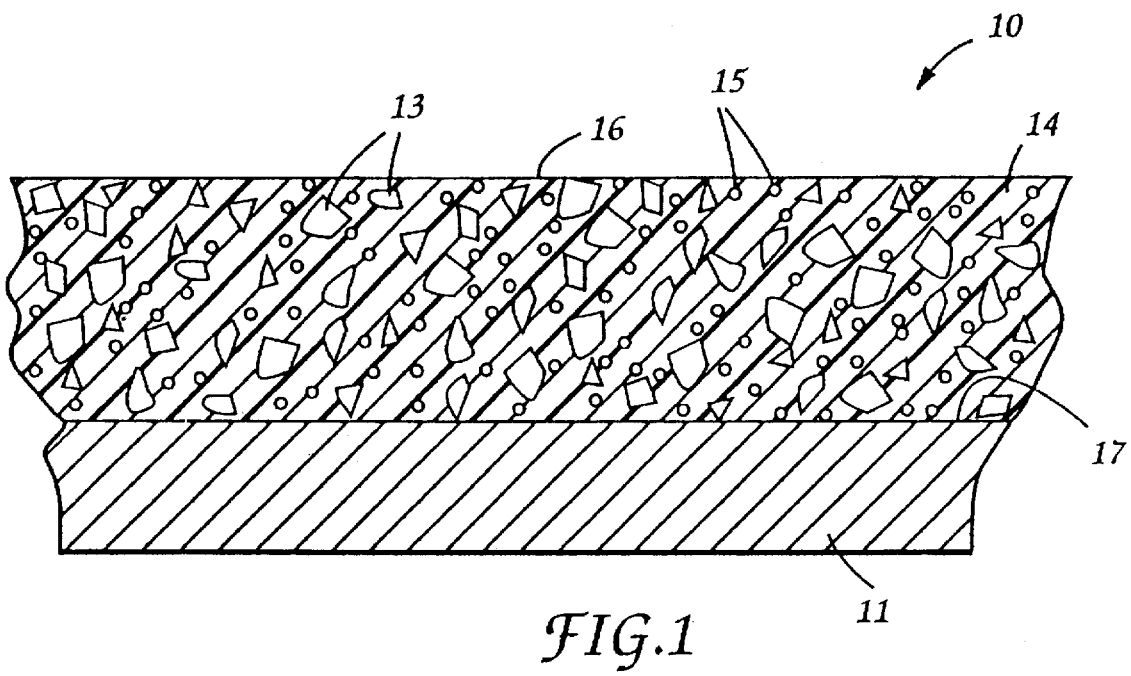
FIG. 1 is a section view, enlarged, of an abrasive article embodiment of this invention.

Compounds functional as reactive diluents and therefore useful in the present invention in abrasive articles are preferably made by a generic process which is detailed in the examples for each particular compound.

As explained further herein below, compounds useful in the invention facilitate solubilization of polar resins, and generally have an effect on the properties of cured compositions. In general, compounds useful in the invention function to increase the glass transition temperature of cured compositions in which they are employed. This in turn translates into a more thermally stable cured composition, which can be important in some applications, such as when the inventive compositions are used to form coated abrasive articles.

Useful compounds as reactive diluents comprise at least one ethylenically-unsaturated group which copolymerizes or crosslinks with ethylenically-unsaturated groups present in the addition polymerizable resin. Although there is no particular upper limitation on the number of ethylenically-unsaturated groups in each molecule of the inventive compounds (other than viscosity limitations discussed herein), a plurality of (up to about 10) ethylenically-unsaturated groups may be present in the inventive compounds, preferably from about 1 to about 4, and most preferably either 1 or 2 ethylenically-unsaturated groups are present in each reactive diluent molecule.

The non-optional ethylenically-unsaturated group(s) of the inventive reactive diluent compounds are preferably selected from the group consisting of acryloyl, methacryloyl, thioacryloyl, thiomethacryloyl, N-substituted acrylamidoyl and N-substituted methacrylamidoyl. Particularly preferred are compounds wherein the ethylenically unsaturated group is —O—C(=O)—CH=CH$_2$ or —NR—C(=O)—CH=CH$_2$, wherein R is selected from the group consisting of —H and C$_x$H$_{2x+1}$, and x ranges from 1 to 10 inclusive. Substituents on nitrogen of (meth)acrylamidoyl ethylenically-unsaturated groups are preferably selected from the group consisting of H, C$_x$H$_{2x+1}$, and —C$_x$H$_{2x}$—Y—C(=W)—CR$^3$=CH$_2$, wherein x is as defined herein, W is preferably selected from the group consisting of NR$^3$, O, and S, and Y is preferably selected from the group consisting of O, S, and NR$^3$.

Compounds useful in the invention for use as reactive diluents preferably comprise one or two organic linking radicals (in the case of compounds within general formulas (I), (II), (IV) and (V) when n is 1 or 2) or only one organic linking radical (compounds within general formula (III)) which links the ethylenically-unsaturated group(s) to a polar organic moiety. The linking radicals may include as part of their structure either one or two R$^1$ radicals, depending on the particular compound.

The R$^1$ radicals are preferably selected from the group consisting of organic radicals devoid of reactive groups other than optional ethylenically-unsaturated groups, and are preferably selected from the group consisting of organic radicals having from 1 to 12 carbon atoms. More preferably, the R$^1$ radical(s) of compounds within general formulas (I)–(V) are selected from the group consisting of —CH$_2$—, —CH$_2$—CH$_2$—, —CH$_2$—CH(OC(=O)CR$^3$=CH$_2$)—CH$_2$—, —O—CH$_2$—CH$_2$—, and mixtures thereof. In the case of compounds within general formulas (I)–(V) having more than one R$^1$, the R$^1$ radicals are independently selected and may be the same or different. The constitution of the R$^1$ radicals in each molecule of the inventive reactive diluents are not particularly limited (within the viscosity limitations discussed herein).

Compounds useful as reactive diluents within general formulas (I)–(V) comprise at least one polar functional group or moiety. In general formula (I) the polar moiety is generally denoted as the aromatic C=W; in general formula (II) the aromatic ring having pendant R$^2$ and R$^4$; in general formula (III) the succinimide moiety including W and Q; and in general formulas (IV) and (V), the R$^2$-(Het) moiety. The polar functional group or moiety facilitates the solubilization of polar resins, such as aminoplast resins, in the reactive diluent compounds.

In compounds within general formulas (I), (II), (IV), and (V) herein, R$^2$ is selected from the group consisting of —H, organic radicals devoid of reactive groups other than optional ethylenically-unsaturated groups (preferably selected from the group consisting of radicals having from 1 to 12 carbon atoms), and moieties which do not substantially terminate polymerization of ethylenically-unsaturated groups. Preferred structures are those wherein m is 2 and the R$^2$ groups together form a group selected from the group consisting of fused aromatic, fused cycloaliphatic, fused bicycloaromatic, and fused heterocyclic rings. Preferably the fused rings have from 1 to about 7 ring atoms. R$^2$ is also preferably selected from the group consisting of amino, halo, alkoxy and carboxyl, with the proviso that such ring substituent groups are selected such that they do not interfere with subsequent free-radical polymerization of the inventive compound(s).

Preferably, the R$^2$ groups of compounds within general formulas (I), (II), (IV), and (V), and the Q group of compounds within general formula (III), as the case may be, are selected to form polar groups selected from the group consisting of appropriately substituted monocyclic aromatic rings, monocyclic aliphatic rings, pyrrole, furan, thiophene, imidazole, pyrazole, thiazole, oxazole, pyrrolidone, morpholine, N-acryloylpiperazine, N-acryloylpiperidine, hydrogenated and partially hydrogenated derivatives thereof, and mixtures thereof, appropriately substituted with one or more linking groups. Most preferably, R$^2$ is selected from the group consisting of a phenolic compound substituted at the 2- position with a linking radical and a phenolic compound substituted at the 2- and 6- positions with a linking radical.

There is sometimes no clear distinction between the polar group or moiety and the linking group of the compounds within general formulas (I) and (V), these categorizations being merely used for convenience. For example, the linking portion of useful compounds within the invention may have polar moieties. Polar moieties are formed in compounds within general formula (I), (IV), and (V) when W, Y and X are selected to form polar groups selected from the groups including, but not limited to, —C(=)O—, —C(=O)NR$^3$—, —C(=O)S—, —C(=S)O—, and —C(=S)NR$^3$—. Polar moieties are also formed when W is O in general formula (III), thus forming cyclic imides, and Q is selected to provide heterocyclic rings selected from the group comprising pyrrole, furan, thiophene, imidazole, pyrazole, thiazole, oxazole, N-acryloylpiperazine, N-acryloylpiperidine, hydrogenated and partially hydrogenated derivatives thereof, and mixtures thereof. The terms "cycloaliphatic" and "bicycloaliphatic" are meant to include ring structures having 3 to 10 and 3 to 20 carbon atoms, respectively, and which may have some degree of unsaturation, for example a $C_5$ ring may have one —C=C—. Particularly preferred reactive diluent compounds are those within general formulas (I), (IV) and (V) which include linking groups having polar moieties, such as when W is O and X and Y are selected from O and $NR_3$, thus forming —C(=O)O—, —C(=O)NR$^3$—, respectively.

Other particularly preferred reactive diluents are those within general formula (III) where a cyclic imide is fused to a group selected from a carbocyclic ring (i.e., phthalimide), a furan ring, a thiophene ring, a thiazole ring, and an oxazolidinone ring, because these polar functional groups provide sufficient solubility of resins in the reactive diluent, are easily prepared, and are thermally stable.

Particularly preferred compounds useful as reactive diluents in the present invention are selected from the group consisting of:

(i) compounds within general formula (VI):

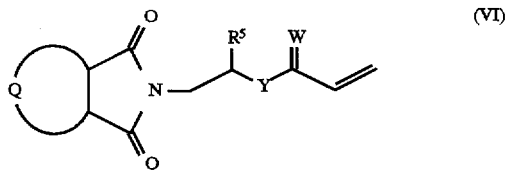

(VI)

wherein:
Q is selected from the group consisting of cycloaliphatic residues, bicycloaliphatic residues, and aromatic residues, wherein the residues are devoid of ring substituents which substantially interfere with free radical polymerization of ethylenically unsaturated groups;

W is selected from the group consisting of NR$^7$, O, and S;
Y is selected from the group consisting of O, S, and NR$^6$;
R$^5$ is selected from the group consisting of —H, —(R$^1$)$_t$, —Y—C(=W)—CR$_3$=CH$_2$, and $C_1$-$C_{12}$ (inclusive) organic radicals;
R$^6$ is selected from the group consisting of H, —$C_xH_{2x+1}$, —C(=W)—CH=CH$_2$, and —$C_xH_{2x}$—O—C(=W)—CH=CH$_2$; R$^7$ is selected from the group consisting of H and —$C_xH_{2x+1}$;
x ranges from 1 to 10 inclusive, wherein R$^6$ and R$^7$ may be the same or different; and
t is 0 or 1;

(ii) compounds within general formula (VII):

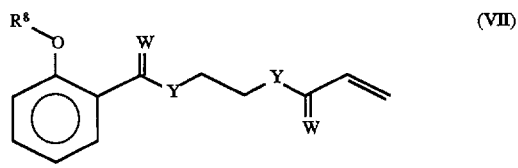

(VII)

wherein:
each W is selected independently and can be the same or different, W being selected from the group consisting of NR$^7$, O, and S;
each Y is selected independently and can be the same or different, Y being selected from the group consisting of O, S, and NR$^6$;
R$^6$ is selected from the group consisting of H, —$C_xH_{2x+1}$, —C(=W)—CH=CH$_2$, —$C_xH_{x2}$—O—C(=W)—CH=CH$_2$;
R$^7$ is selected from the group consisting of H, —$C_xH_{2x+1}$;
R$^8$ is selected from the group consisting of H and —C(=W)—CH=CH$_2$; and
x ranges from 1 to 10 inclusive, wherein R$^6$ and R$^7$ may be the same or different;

(iii) compounds within general formula (VIII):

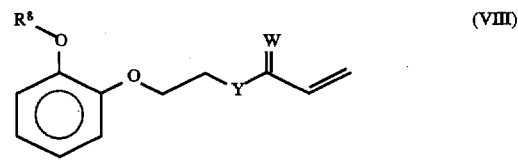

(VIII)

wherein:
W is selected from the group consisting of NR$^7$, O, and S;
Y is selected from the group consisting of O, S, and NR$^6$;
R$^6$ is selected from the group consisting of H, —$C_xH_{2x+1}$, —C(=W)—CH=CH$_2$, and —$C_xH_{2x}$—O—C(=W)—CH=CH$_2$;
R$^7$ is selected from the group consisting of H and —$C_xH_{2x+1}$; and
R$^8$ is selected from the group consisting of H and —C(=W)—CH=CH$_2$; and
x ranges from 1 to 10 inclusive, wherein R$^6$ and R$^7$ may be the same or different;

(iv) aromatic compounds within general formula (IX):

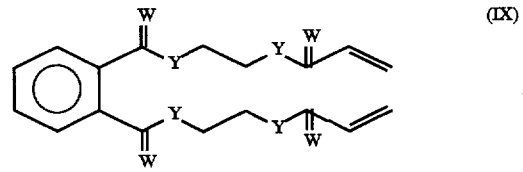

(IX)

wherein:
each W is selected independently and can be the same or different, W being selected from the group consisting of NR$^7$, O, and S;
each Y is selected independently and can be the same or different, Y being selected from the group consisting of O, S, and NR$^6$;
R$^6$ is selected from the group consisting of H, —$C_xH_{2x+1}$, —C(=W)—CH=CH$_2$, and —$C_xH_{2x}$—C(=W)—CH=CH$_2$;
R$^7$ is selected from the group consisting of H and —$C_xH_{2x+1}$,
x ranges from 1 to 10 inclusive, wherein R$^6$ and R$^7$ may be the same or different;

(v) heterocyclic compounds within general formula (X):

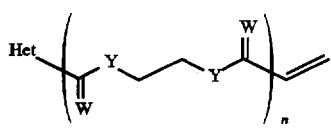

wherein:

each W is selected independently and can be the same or different, W being selected from the group consisting of $NR^7$, O, and S;

each Y is selected independently and can be the same or different, Y being selected from the group consisting of O, S, and $NR^6$;

Het is a heterocyclic ring selected from the group consisting of furan, thiophene, thiazole, oxazole, imidazole, and oxazoline;

n is an integer ranging from 1 to about 4;

$R^6$ is selected from the group consisting of H, $—C_xH_{2x+1}$, $—C(=W)—CH=CH_2$, and $—C_xH_{2x}—O—C(=W)—CH=CH_2$;

$R^7$ is selected from the group consisting of H and $—C_xH_{2x+1}$; and x ranges from 1 to 10 inclusive, wherein $R^6$ and $R^7$ may be the same or different; and (vi) heterocyclic compounds within general formula (XI):

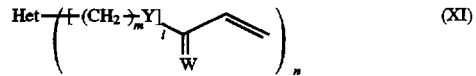

wherein:

each W is selected independently and can be the same or different, W being selected from the group consisting of $NR^7$, O, and S;

each Y is selected independently and can be the same or different, Y being selected from the group consisting of O, S, and $NR^6$;

Het is a heterocyclic ring selected from the group consisting of furan, pyrrolidone, morpholine, thiophene, thiazole, oxazole, imidazole, and oxazoline;

m=1 or 2;

n is an integer ranging from 1 to about 4; and $R^6$ is selected from the group consisting of H, $—C_xH_{2x+1}$, $—C(=W)—CH=CH_2$, and $—C_xH_{2x}—O—C(=W)—CH=CH_2$;

$R^7$ is selected from the group consisting of H and $—C_xH_{2x+1}$; and l is 0 or 1; and x ranges from 1 to 10 inclusive, wherein $R^6$ and $R^7$ may be the same or different; and mixtures thereof.

Other preferred compounds useful as reactive diluents and within the invention are selected from the group consisting of:

(vii) carbocyclic imides within general formula (XII):

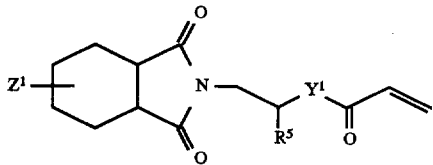

wherein:

$R^1$ and $R^3$ are defined as in structure (I) above;

$Z^1$ is selected from the group consisting of H, $—C_xH_{2x+1}$, and $—CH_2—$ group bridging $C_3$-$C_6$ (inclusive);

$Y^1$ is selected from the group consisting of $NR^6$ and O;

$R^5$ is selected from the group consisting of —H, $—(R^1)$, $—Y—C(=O)—CR_3=CH_2$, and $C_1$-$C_{12}$ (inclusive) organic radicals;

$R^6$ is selected from the group consisting of H, $—C_xH_{2x+1}$, $—C(=O)—CH=CH_2$, and $—C_xH_{2x}—O—C(=O)—CH=CH_2$; t is 0 or 1; and x ranges from 1 to 10 inclusive, wherein $R^6$ and $Z^1$ may be the same or different;

(viii) salicylic acid derivatives within general formula (XIII):

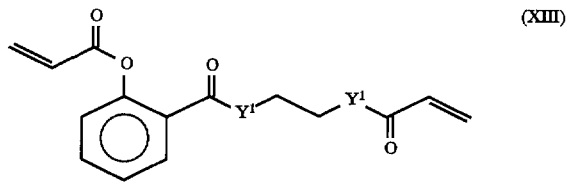

wherein:

each $Y^1$ is independently selected from the group consisting of $NR^6$ and O;

$R^6$ is selected from the group consisting of H, $—C_xH_{2x+1}$, $—C(=O)—CH=CH_2$, $—C_xH_{2x}—O—C(=O)—CH=CH_2$; and x ranges from 1 to 10 inclusive, wherein each $R^6$ may be the same or different;

(ix) catechol derivatives within general formula (XIV):

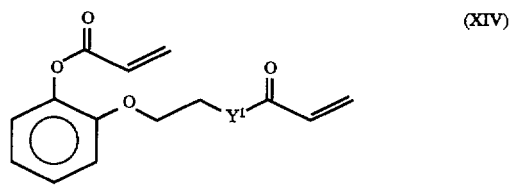

wherein:

$Y^1$ is selected from the group consisting of $NR^6$ and O;

$R^6$ is selected from the group consisting of H, $—C_xH_{2x+1}$, $—C(=O)—CH=CH_2$, and $—C_xH_{2x}—O—C(=O)—CH=CH_2$; and x ranges from 1 to 10 inclusive, wherein each $R^6$ may be the same or different;

(x) phthalate esters or phthalamides within general formula (XV):

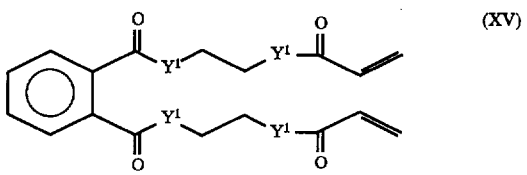

wherein:

each $Y^1$ is independently selected from the group consisting of $NR^6$ and O;

$R^6$ is selected from the group consisting of H, $—C_xH_{2x+1}$, $—C(=O)—CH=CH_2$, and $—C_xH_{2x}—O—C(=O)—CH=CH_2$; and x ranges from 1 to 10 inclusive, wherein each $R^6$ may be the same or different;

(xi) heterocyclic acid esters or heterocyclic acid amides within general formula (XVI):

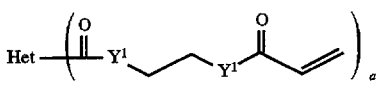

wherein:
each $Y^1$ is independently selected from the group consisting of $NR^6$ and O;
a is 1 or 2;
Het is selected from the group consisting of furanyl, thienyl, 3-alkyl-2-thiazinyl, and imidazolyl;
$R^6$ is selected from the group consisting of H, $-C_xH_{2x+1}$, $-C(=O)-CH=CH_2$, and $-C_xH_{2x}-O-C(=O)-CH=CH_2$; and
x ranges from 1 to 10 inclusive, wherein each $R^6$ may be the same or different; and (xii) heterocyclic acrylates and heterocyclic acrylamides within general formula (XVII):

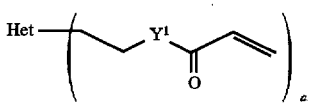

wherein:
each $Y^1$ is independently selected from the group consisting of $NR^6$ and O;
a is 1 or 2;
Het is selected from the group consisting of furanyl, morpholinyl, pyrrolidonyl, thienyl, 3-alkyl-2-thiazinyl, imidazolyl, oxazolidin-2-on-5-yl, and mixtures thereof; and
$R^6$ is selected from the group consisting of H, $-C_xH_{2x+1}$, $-C(=O)-CH=CH_2$, and $-C_xH_{2x}-O-C(=O)-CH=CH_2$; and
x ranges from 1 to 10 inclusive, wherein each $R^6$ may be the same or different.

Specifically preferred compounds useful as reactive diluents include:
2,6-di(acryloyloxymethyl)acryloyloxy-p-cresol;
2-(acryloyloxyethoxy)acryloyloxyphenol;
N,N'-di(acryloyloxyethyl)-N,N'-dimethyl-o-phthalamide;
N-(acryloyloxyethoxyethyl)hexahydrophthalimide;
N-(2,3-di(acryloyloxy)propyl)hexahydrophthalimide;
2-(acryloyloxyethyl)thienoate;
2-(acryloyloxyethyl)-3-methylthiazole;
2-(N,N'-di(acryloyloxyethyl))thiophenecarboxamide; and
5-acryloyloxymethyl-oxazolidin-2-one.

Methods of production of compounds suitable for use as reactive diluents are presented in the Examples section.

Solvent Power

Compounds within general formulas (I)–(V) useful as reactive diluents exhibit particularly excellent solvency towards radiation curable aminoplast resins having unsaturation positioned $\alpha,\beta$ to the carbonyl groups, such as those described in U.S. Pat. Nos. 4,903,440 (the '440 patent), 5,055,113 (the '113 patent), and 5,236,472 (the '472 patent), all assigned to the assignee of the present application. The inventive compounds also exhibit excellent solvency toward phenolic resins, urethane resins, oligoacrylate resins and epoxy resins. Among these resins, the aminoplast resins are known to be quite insoluble in most known acrylate-functional reactive diluents. Specifically, a compound useful as a reactive diluent preferably dissolves at least its own weight of acrylamidomethylated phenol (hereinafter referred to as "AMP") described in the '440 patent, or acrylamidomethyl novolak resin (hereinafter referred to as "AMN") described in the '472 patent. Thus, as an example, at least 10 grams of acrylamidomethyl phenol preferably dissolves completely in 10 grams of an inventive compound at 20° C. in order for the inventive compound to be considered as exhibiting sufficient solvency towards aminoplast resins. More preferably, compounds useful in the invention dissolve at least 120% of their weight of aminoplast resins, and, most preferably, compounds useful in the invention dissolve at least 150% of their weight of aminoplast resins, in order for the resulting cured resin formulations to exhibit the required combination of hardness and durability.

Viscosity

In order to be useful in the preparation of cured resin systems, compounds useful in the invention as reactive diluents and within general formulas (I)–(V) typically and preferably exhibit viscosities ranging from about 30 centipoise (cps) to about 2000 cps at about 20° C., as measured by a Brookfield viscometer model number LVF, no. 4 spindle, 60 rpm, at 25° C., as described in American Society of Testing and Materials (ASTM) test no. 1824-87. Preferably, compounds useful in producing the abrasive articles of the invention exhibit viscosities ranging from about 30 cps to about 1000 cps at about 20° C., and, most preferably, viscosities ranging from about 30 cps to about 500 cps at about 20° C.

While the viscosity of the reactive diluent compound itself is critical, the viscosity and rheological properties of resin formulations comprising the reactive diluent compounds and resins such as aminoplasts, epoxy resins, and the like, are also critical to the ability to produce abrasive articles of the invention. Thus, formulations comprising about 50 parts by weight aminoplast resin and about 50 parts by weight reactive diluent(s) preferably exhibit viscosities in the range of from about 30 cps to about 5000 cps, more preferably from about 30 to about 2000, in order to be readily coatable on substrates known in the abrasive materials art using standard coating methods and apparatus known in the abrasive materials art.

Resin Systems

Compounds within general formulas (I)–(V) useful as reactive diluents are used in conjunction with known resin materials to prepare, e.g., rapidly curable make coatings and size coatings for abrasive constructions. In these applications, a coatable composition comprising the resin and reactive diluent, along with optional photoinitiators, thermal initiators, fillers, pigments and other additives known in the art, is prepared and coated onto a substrate. The coating is then exposed to the appropriate energy source(s) sufficient to cure the coatings, typically and preferably radiation energy and, optionally, thermal energy.

As previously mentioned, precursors of conventional thermally curable condensation resins, such as phenol, formaldehyde, urea, melamine and furfural can be admixed with the above-described coatable compositions. However, the preferred precursor composition comprises a radiation-energy-curable aminoplast resin as described in the above-mentioned '440, '113 and '472 patents, the disclosures of which are incorporated by reference herein for the purpose of disclosure of radiation-curable aminoplast resins.

Radiation-curable aminoplast resins having ethylenic unsaturation positioned $\alpha,\beta$ from a carbonyl group, which are also interchangeably referred to herein as "aminoplasts", are obtained by reacting amino-functional compounds with aldehydes to produce compounds having hydroxyalkyl groups. The hydroxyalkyl groups are further reacted with hydroxyalkyl esters of acrylic or methacrylic acid to form aminoplasts with pendant groups having unsaturation positioned $\alpha,\beta$ from the carbonyl group. In the presence of a suitable initiator, the unsaturated aminoplasts can be cured by either thermal or irradiative means (or a combination thereof) to form a hard, crosslinked binder resin which finds utility in abrasive articles. The most common and preferred aldehyde is formaldehyde, which reacts with the amino group (—NHR) to produce compounds having hydroxymethyl groups. The R substituent of the —NHR group is typically and preferably a hydrogen or a hydrocarbon, which may be substituted or unsubstituted, but, if substituted, the substituent or substituents should be those that do not inhibit or prevent polymerization.

Preferably, aminoplast resins useful as curable abrasive binders have an average of at least 1.1 pendant groups per molecule having ethylenic unsaturation positioned $\alpha,\beta$ from a carbonyl group, also referred to herein as "$\alpha,\beta$-unsaturated carbonyl groups". Useful $\alpha,\beta$-unsaturated carbonyl groups include acrylate, methacrylates, acrylamides and methacrylamides, and mixtures thereof. These aminoplast resins polymerize via free-radical polymerization at the site of the $\alpha,\beta$-unsaturated carbonyl groups and are curable by either heat or irradiation.

In addition, the aminoplasts can also contain pendant amino (—NHR) or hydroxyl (—OH) functional groups, where the R substituent is typically and preferably a hydrogen or a hydrocarbon, which may be substituted or unsubstituted, but, if substituted, the substituent or substituents should be those that do not inhibit or prevent polymerization. Preferred examples of the R substituent include alkyl (e.g., methyl, ethyl, and the like), aryl (e.g., phenyl and the like), alkoxy and carbonyl.

Preferably, resin systems for preparing binders for abrasives are selected from the group consisting of:

A. aminoplast resins having on average at least 1.1 pendant $\alpha,\beta$-unsaturated carbonyl groups per molecule, B. aminoplast resins having on average at least 1.1 pendant $\alpha,\beta$-unsaturated carbonyl groups per molecule and at least one pendant —NHR or —OH functional group per molecule, and C. condensation curable resins and aminoplast resins having on average at least 1.1 pendant $\alpha,\beta$-unsaturated carbonyl groups per molecule and at least one pendant —NHR or —OH functional group per molecule.

Most preferably, aminoplast resins used in conjunction with reactive diluents of the invention are selected from the group consisting of acrylamidomethyl phenol, acrylamidomethyl novolak, melamine acrylate resin, bis (acrylamidomethyl) ether, tetra(acrylamidomethyl) glycoluril, N-(hydroxymethyl)acrylamide, and mixtures thereof.

Examples of other useful addition polymerizable binder precursors include acrylated urethanes, acrylated epoxies, isocyanurate derivatives having at least one pendantlacrylate group, isocyanate derivatives having at least one pendant acrylate group, vinyl ethers, epoxy resins and mixtures and combinations thereof. The term acrylate is meant to encompass acrylates and methacrylates.

Acrylated urethanes are diacrylate esters of hydroxy terminated isocyanate ("NCO") extended polyesters or polyethers. Examples of commercially available acrylated urethanes include those known under the trade designations UVITHANE 782, available from Morton Thiokol Chemical, and EBECRYL 6600, EBECRYL 8400, and EBECRYL 8805, available from UCB Radcure, of Louisville, KY.

Acrylated epoxies are diacrylate esters of epoxy resins, such as the diacrylate esters of bisphenol A epoxy resin. Examples of commercially available acrylated epoxies include those known under the trade designations EBECRYL 3500, EBECRYL 3600, and EBECRYL 3700, also available from UCB Radcure.

Ethylenically unsaturated resins include both monomeric and polymeric compounds that contain atoms of carbon, hydrogen and oxygen, and optionally, nitrogen and the halogens. Oxygen or nitrogen atoms or both are generally present in ether, ester, urethane, amide, and urea groups. Ethylenically unsaturated compounds preferably have a molecular weight of less than about 4,000 and are preferably esters made from the reaction of compounds containing aliphatic monohydroxy groups or aliphatic polyhydroxy groups and unsaturated carboxylic acids, such as acrylic acid, methacrylic acid, itaconic acid, crotonic acid, isocrotonic acid, maleic acid, and the like. Representative examples of ethylenically unsaturated compounds useful in the invention include methyl methacrylate, ethyl methacrylate, ethylene glycol diacrylate, ethylene glycol dimethacrylate, hexanediol diacrylate, triethylene glycol diacrylate, trimethylolpropane triacrylate, glycerol triacrylate, pentaerythritol triacrylate, pentaerythritol trimethacrylate, pentaerythritol tetraacrylate and pentaerythritol tetramethacrylate. Other useful ethylenically unsaturated compounds include monoallyl, polyallyl, and polymethallyl esters and amides of carboxylic acids, such as diallyl phthalate, diallyl adipate, and N,N-diallyladipamide. Still other useful nitrogen containing compounds include tris(2-acryloyloxyethyl)-isocyanurate, 1,3,5-tri(2-methacryloxyethyl)-s-triazine, acrylamide, methylacrylamide, N-methylacrylamide, N,N-dimethylacrylamide, N-vinylpyrrolidone, and N-vinylpiperidone.

Isocyanurate derivatives having at least one pendant acrylate group and isocyanate derivatives having at least one pendant acrylate group are further described in U.S. Pat. No. 4,652,274 incorporated herein by reference. The preferred isocyanurate material is the triacrylate of tris(hydroxyethyl) isocyanurate.

Epoxy resins have at least one oxirane group and are polymerized by ring opening. Useful epoxy resins include monomeric epoxy resins and oligomeric epoxy resins. Examples of some preferred epoxy resins include 2,2-bis[4-(2,3-epoxypropoxy)phenyl]propane] (diglycidyl ether of bisphenol A) and commercially available materials known under the trade designation EPON 828, EPON 1004 and EPON 1001F available from Shell Chemical Co., and those known under the trade designations DER-331, DER-332 and DER-334 available from Dow Chemical Co. Other suitable epoxy resins include glycidyl ethers of phenol-formaldehyde novolak resins (e.g., those known under the trade designations DEN-431 and DEN-438 available from Dow Chemical Co.).

The epoxy resins useful in the invention can polymerize via a cationic mechanism with the addition of an appropriate cationic curing agent. Cationic curing agents generate an acid source to initiate the polymerization of an epoxy resin. These cationic curing agents can include a salt having an onium cation and a halogen containing complex anion of a metal or metalloid. Other cationic curing agents include a salt having an organometallic complex cation and a halogen containing complex anion of a metal or metalloid which are further described in U.S. Pat. No. 4,751,138 incorporated herein by reference (column 6 line 65 to 9 line 45). Other useful cationic curing agents include organometallic salts and onium salts described in U.S. Pat. No. 4,985,340 (column 4, line 65 to column 14, line 50); European Patent Applications 306,161 and 306,162, both published Mar. 8, 1989, all incorporated by reference. Still other cationic curing agents include an ionic salt of an organometallic complex in which the metal is selected from the elements of Periodic Group IVB, VB, VIB, VIIB and VIIIB which are described in European Patent Application 109,581, published Nov. 21, 1983, incorporated herein by reference.

Curing and Cure Rate

The rate at which addition polymerizable reactive diluents cure is an important measure of their utility in resin formulations for abrasive articles. If the reactive diluent cures at a rate significantly slower than the addition polymerizable resin, the resulting cured formulation may have more than one phase and may be unusable as, e.g., an abrasive binder. In addition, a slow-curing reactive diluent will decrease processing speed, which may unnecessarily increase the cost of the final abrasive product. If the addition polymerizable reactive diluent cures at a rate significantly faster than the addition polymerizable resin, the resulting cured material may be biphasic and may not exhibit the overall hardness required for an abrasive product.

Aminoplast resins are typically and preferably cured by exposure to ultraviolet lamps operating at 236 watt/cm, operating in the range of 200 to 700 nanometers, preferably 250 to 400 nanometers wavelength, at a web rate ranging from about 3 to about 100 meters/minute. Of course, it is understood that the rate of curing with radiation energy varies according to the binder thickness as well as the density and nature of the composition, and with the intensity of the radiation.

In general, during the manufacture of an abrasive article in accordance with the present invention, an addition polymerizable binder precursor composition is applied to a substrate and at least partially cured or polymerized. This polymerization is generally initiated upon exposure to an energy source. Examples of energy sources include thermal energy and radiation energy. The amount of energy required depends upon several factors such as the binder precursor chemistry, the thickness of the applied binder precursor coating, the amount and type of particulate matter in the binder precursor, if any, and the amount and type of other optional additives. For thermal curing, temperatures may range from about 30° to about 150° C., more preferably between about 40° and 120° C. The exposure time for thermal curing may range from about 5 minutes to over 24 hours.

Suitable radiation energy sources include electron beam, ultraviolet light and/or visible light. Electron beam irradiation, which is also known as ionizing radiation, can be used at an energy level ranging from about 0.1 to about 10 Mrad, preferably at an energy level of about 1 to about 10 Mrads. Ultraviolet radiation refers to non-particulate radiation having a wavelength ranging from about 200 to about 400 nanometers, preferably within the range of about 250 to about 400 nanometers. It is preferred that the ultraviolet light have an intensity of about 118 to about 236 watts/cm. Visible radiation refers to non-particulate radiation having a wavelength within the range of about 400 to about 800 nanometers, preferably in the range of about 400 to about 550 nanometers.

Examples of free radical thermal initiators include peroxides, e.g., benzoyl peroxide, azo compounds, benzophenones and quinones. For either ultraviolet or visible light energy source, this curing agent is sometimes referred to as a photoinitiator. Examples of initiators, that when exposed to ultraviolet light generate a free radical source, include but are not limited to those selected from the group consisting of organic peroxides, azo compounds, quinones, benzophenones, nitroso compounds, acyl halides, hydrazones, mercapto compounds, pyrylium compounds, triacylimidazoles, bisimidazoles, chloroalkytriazines, benzoin ethers, benzil ketals, thioxanthones, and acetophenone derivatives, and mixtures thereof. Examples of initiators that when exposed to visible radiation generate a free radical source, can be found in U.S. Pat. No. 4,735,632, entitled Coated Abrasive Binder Containing Ternary Photoinitiator System incorporated herein by reference. One preferred free radical initiator is 2,2-dimethoxy-1,2-diphenyl-1-ethanone, commercially available from Ciba-Geigy Corporation, Hawthorne, NY, under the trade designation IRGACURE 651.

Traditionally, abrasive binder systems are cured thermally. Thermal curing typically requires long heating times at elevated temperatures, a process which may add expense to the abrasive and may contribute to environmental pollution when coating solvents are evaporated, or may require that additional steps be taken, using additional equipment and resources, to recover evaporated solvent. A major advantage of the use of reactive diluent compounds within general formula (I) in 100%-radiation-energy cured binder systems is the reduction or elimination of these wasteful and costly processing steps.

Comparative hardness testing of reactive diluent compounds with thermally curable, condensable resin precursors requires measuring the effect of a post-radiation heating cycle. Thus, compositions comprising reactive diluents within general formula (I) and addition polymerizable resins were cured by ultraviolet radiation and the Knoop hardness of the cured compositions was tested (see below). Then, the radiation-cured samples were heated an additional one hour at 140° C., and any difference in hardness was noted.

Addition polymerizable reactive diluents useful in this invention can be solely used as the abrasive article binder. However, it is generally preferred that the addition polymerizable reactive diluent be combined or blended with addition polymerizable resin precursors and this resin precursor blend be utilized in the production of the abrasive article binder. It is most preferred that the addition polymerizable reactive diluents within general formula (I) be blended with addition polymerizable resin precursors, so that during curing the reactive diluent can polymerize with the resin.

Optionally, thermally curable condensation-type resin precursors, such as phenol and formaldehyde, widely used in abrasive article binders because of their thermal properties, availability, cost and ease of handling, may be blended with the addition polymerizable precursors. There are two types of phenolic resins, resole and novolak. Resole phenolic resins have a molar ratio of formaldehyde to phenol greater than or equal to one to one, typically between 1.5:1.0 to 3.0:1.0. Novolak resins have a molar ratio of formaldehyde to phenol of less than one. Examples of commercially available phenolic resins include those known by the tradenames DUREZ and VARCUM from Occidental Chemicals Corp.; RESINOX from Monsanto; and AROFENE and AROTAP from Ashland Chemical The binder can further comprise optional additives, such as, for example, fillers (including grinding aids), fibers, lubricants, wetting agents, thixotropic materials, surfactants, pigments, dyes, anti-static agents, coupling agents, plasticizers and suspending agents. The amounts of these materials are selected to provide the properties desired. The use of these can affect the erodability of the abrasive composite. In some instances an additive is purposely added to make the abrasive composite more erodable, thereby expelling dulled abrasive particles and exposing new abrasive particles. One class of additives found useful for this purpose are kaolin and other clays, as more particularly disclosed in assignee's copending application Ser. No. 07/999,097, filed Dec. 31, 1992.

The term filler also encompasses materials that are known in the abrasive industry as grinding aids. A grinding aid is defined as particulate material that the addition of which has a significant effect on the chemical and physical processes of abrading which result in improved performance. In particular, it is believed in the art that the grinding aid will either 1) decrease the friction between the abrasive particles and the workpiece being abraded, 2) prevent the abrasive particle from "capping", i.e. prevent metal particles from becoming welded to the tops of the abrasive particles, 3) decrease the interface temperature between the abrasive particles and the workpiece 4) decrease the grinding forces. Grinding aids encompass a wide variety of different materials and can be inorganic or organic based. Examples of chemical groups of grinding aids include waxes, organic halide compounds, halide salts and metals and their alloys. The organic halide compounds typically will break down during abrading and release a halogen acid or a gaseous halide compound. Examples of such materials include chlorinated organic compounds like tetrachloronaphthalene, pentachloronaphthalene, and polyvinyl chloride. Examples of halide salts include sodium chloride, potassium cryolite, sodium cryolite, ammonium cryolite, potassium tetrafluoroborate, sodium tetrafluoroborate, silicon fluorides, potassium chloride, and magnesium chloride. Examples of metals include, tin, lead, bismuth, cobalt, antimony, cadmium, iron, and titanium. Other miscellaneous grinding aids include sulfur, organic sulfur compounds, graphite and metallic sulfides.

Examples of antistatic agents include graphite, carbon black, vanadium oxide, humectants, conductive polymers and the like. These antistatic agents are disclosed in U.S. Pat. Nos. 5,061,294; 5,137,542 and 5,203,884 incorporated herein by reference.

A coupling agent can provide an association bridge between the binder precursor and the filler particles or abrasive particles. Examples of useful coupling agents include silanes, titanates and zircoaluminates. One preferred silane coupling agent is γ-methacryloxypropyltrimethoxysilane, known under the trade designation A-174, from Union Carbide. U.S. Pat. No. 4,871,376 (DeWald) describes reducing viscosity of resin/filler dispersions by utilizing a silane coupling agent. This patent is incorporated by reference for its teaching of lowering viscosity of resin/filler dispersions using coupling agents. The binder precursor compositions typically and preferably contain from about 0.01 to 3 weight percent coupling agent, based on weight of filler and/or abrasive particles.

Dynamic Mechanical Analysis

Some of the benefits of adding the compounds within the above formulas (I)–(V) to addition polymerizable compositions may be determined through an analytical technique known as "dynamic mechanical analysis" ("DMA"). Specifically, the degree of curing, molecular weight distribution, phase separation, and glass transition temperature ("$T_g$") of cured compositions may be investigated.

In a typical DMA test a sample of composition to be tested is used to saturate a glass fiber cloth, and the composition cured using an ultraviolet lamp. The composite is then placed in tension held by a film-fiber fixture and placed in an analyzing instrument. The sample is typically subjected to a stepwise temperature increase ("temperature sweep"), usually from about 0° C. to about 250° C. At various temperature points, measurements of energy loss and energy storage in the composition are measured to determine the "storage modulus", typically denoted E', which may be plotted versus temperature. In general the storage modulus for a material decreases with temperature. Increases in E' accompany curing reactions and in most cases is not desired. Also measured is another parameter, (E"), which is defined as the loss modulus. The ratio (E"/E'), a unitless parameter typically denoted "tan δ", may also be plotted versus temperature. The maximum point of the tan δ curve (point where the slope is zero), if well defined, takes place at the $T_g$ of the composition. By comparing the analytical results of a blend with the results obtained from a sample of resin only (both samples having a small percentage of photoinitiator added thereto), the increase in $T_g$ may be determined, as well as the molecular weight distribution and degree of phase separation.

For compounds within general formulas (I)–(V), it is preferred that the compound increase $T_g$ of the resin by at least about 10° C., more preferably at least about 50° C. Compounds outside of the invention will typically have a flat, bimodal or other not well defined maximum for tan δ, and thus the $T_g$ will not be well defined. It is preferred that the molecular weight distribution be narrow. If the distribution is wide the tan δ peak will be broad. Compounds within the invention should also prevent or reduce phase separation of the compositions.

Backing Materials for Coated Abrasive Articles

Backings useful in this invention for the production of coated abrasives typically and preferably have a front and a back surface and can be selected from any one of a number of conventional abrasive backings. Examples of such include polymeric film (for example polyester and the like), primed polymeric film, cloth, paper, vulcanized fiber, nonwovens and combinations thereof. Still other useful backings include fibrous reinforced thermoplastic backings like those described in Patent Cooperation Treaty (PCT) application no. WO 93129912, published Jul. 8, 1993, and endless seamless belts such as those described in PCT application no. 9312911, also published Jul. 8, 1993, both of which are incorporated herein by reference. The backing may also contain a treatment or treatments to seal the backing and/or modify some physical properties of the backing. Additionally, the reactive diluents useful in this invention can be utilized as a cloth treatment or a backing treatment.

Abrasive Particles

Examples of abrasive particles suitable for use in the present invention include fused aluminum oxide (which includes brown aluminum oxide, heat treated aluminum oxide and white aluminum oxide), ceramic aluminum oxide, green silicon carbide, silicon carbide, chromia, alumina zirconia, diamond, iron oxide, ceria, cubic boron nitride, garnet and combinations thereof.

The absolute particle size of abrasive particles useful in the invention is not critical and may vary widely from about 0.1 micrometer to about 1500 micrometers. The average particle size is preferably between about 0.1 micrometer to 400 micrometers, more preferably between about 0.1 micrometer to about 100 micrometers, and most preferably between about 0.1 micrometer to about 50 micrometers. It is preferred that the abrasive particles have a MOH hardness of at least about 8, more preferably above 9.

The term "abrasive particles" includes individual abrasive grains and also encompasses multiple individual abrasive grains bonded together to form an abrasive agglomerate. Abrasive agglomerates are further described in U.S. Pat. Nos. 4,311,489; 4,652,275 and 4,799,939, all incorporated herein after by reference for their discussion of abrasive grain agglomerates.

Bonded Abrasives

To make a bonded abrasive, a composition is formulated consisting essentially of a compound within general formulas (I)–(V), abrasive particles, optionally an addition polymerizable resin, and optional modifying agents and particles functioning as rheology modifiers such as amorphous silica. Optionally, coupling agents may also be introduced into the slurry either before or after the slurry is poured into a mold. If a silane coupling agent is used, it is not necessary to coat the mold inner surface with a mold release agent. However, when desired, a mold release material may be coated on the surface of the mold to be exposed to the slurry, such as the mold release known under the trade designation "IMS Silicon Spray Parting Agent", no. S-512. Alternatively, the mold could have a non-stick surface, made of a material such as polytetrafluoroethylene or the like.

The slurry is then poured into the selected mold, and subsequently subjected to curing conditions as previously described. Optionally, pressure may be applied to the system during curing. Once the resin is cured, the resulting bonded abrasive is removed from the mold.

Nonwoven Abrasive Articles

Nonwoven abrasive articles comprise an open, lofty, three-dimensional web of fibers bound together at points where they contact by a binder. The binder of such a construction may be made using a composition comprising a reactive diluent compound within general formulas (I)–(V), optional addition polymerizable resin and optional abrasive particles. Methods of making nonwoven abrasive articles are described in U.S. Pat. No. 2,958,293 (Hoover), which is incorporated herein by reference.

Hoover et al. describe uniform, lofty, open, nonwoven three-dimensional abrasive articles for use in cleaning and polishing floors and other surfaces. Examples of such nonwoven surface treating articles are the nonwoven abrasive pads made according to the teachings of Hoover, et al., mentioned above; McAvoy, U.S. Pat. No. 3,537,121; and McAvoy, et al., U.S. Pat. No. 4,893,439. Hoover et al. describe such nonwoven pads as comprising many interlaced, randomly disposed, flexible, durable, tough, organic fibers which exhibit substantial resiliency and strength upon prolonged subjection to water and oils. Fibers of the web are firmly bonded together at points where they intersect and contact one another by globules of an organic binder, thereby forming a three-dimensionally integrated structure. Distributed within the web and firmly adhered by binder globules at variously spaced points along the fibers may be, and typically are, abrasive particles.

The nonwoven articles of the invention may have a wide range of abrasive quality from very coarse pads for gross removal of surface treatments [stripping or scouring pads containing, for example, as in Example I of Hoover, et al., 180 grit (average particle size about 80 micrometers) silicon carbide abrasive particles] to very finely abrasive or non-abrasive polishing pads (containing, for example, as in Example II of Hoover, et. al., 180 grit and finer flint fines, applied at about half the weight of the silicon carbide of Example I).

U.S. Pat. No. 5,030,496 (McGurran), except for the binders used in the present invention, describes non-woven fibrous surface treating articles. As noted in column 5, lines 61–68, useful abrasive particles depend largely on the application and may range in size anywhere from about grade 24, average particle diameter of about 0.71 mm (or 710 micrometers), to about 1,000 grade, average particle diameter of about 0.01 mm (i.e., about 10 micrometers).

The nonwoven articles of the invention may include melt-bondable fibers, as described in U.S. Pat. No. 5,082,720 (Hayes). The nonwoven abrasive articles of the invention which employ melt-bondable fibers may include abrasive grains having grade ranging from about 36 to about 1000 (average particle size ranging from about 600 to about 10 micrometers).

Lapping Abrasives and Methods of Production

Figure 2:
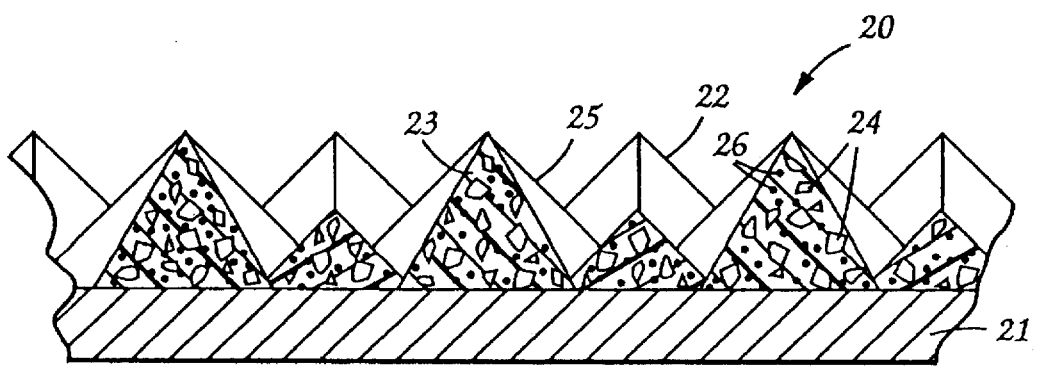
FIG. 2 is a section view, enlarged, representing another abrasive article embodiment of this invention.

Lapping abrasives, examples of which are illustrated in FIGS. 1 and 2, are a type of coated abrasive.

Referring to the drawing figures, FIG. 1 is an illustration (enlarged) of a lapping abrasive article 10 within the invention having a backing 11 having an abrasive coating 16 bonded to at least the front surface 17 of the backing. The abrasive coating 16 comprises a homogeneous mixture of a plurality of abrasive particles 13, a binder 14 and optionally a grinding aid 15. The binder 14 serves also to bond the abrasive coating 16 to the front surface 17 of the backing 11. The abrasive particles are essentially uniformly dispersed throughout the binder and grinding aid mixture.

The lapping abrasive article embodiment illustrated in FIG. 1 may be made by coating a composition within the invention onto the backing by any suitable technique, such as roll coating, gravure coating, and the like, it being understood that a more rough or varied surface may be produced. The composition is then exposed to a radiation source, preferably producing radiation in the UV and/or visible spectrum ranging from about 300 nanometers to about 1000 nanometers, more preferably ranging from about 300 to about 400 nanometers, and other optional energy sources, depending on the resins used, to cure the binder precursors and form an abrasive composite. Alternatively, the coatable composition may be applied to the backing through a screen to create a patterned abrasive surface.

In some instances it is preferred that the abrasive coating be present as precisely shaped abrasive composites, such as illustrated in FIG. 2. In order to make this type of abrasive article, a production tool is generally required.

The production tool contains a plurality of cavities. These cavities are essentially the inverse shape of the abrasive composite and are responsible for generating the shape of the abrasive composites. The dimensions of the cavities are selected to provide the desired shape and dimensions of the abrasive composites. If the shape or dimensions of the cavities are not properly fabricated, the resulting production tool will not provide the desired dimensions for the abrasive composites.

The cavities can be present in a dot like pattern with spaces between adjacent cavities or the cavities can butt up against one another. It is preferred that the cavities butt up against one another. Additionally, the shape of the cavities is selected such that the cross-sectional area of the abrasive composite decreases as the distance from the backing increases.

In each of the methods wherein a patterned tool is coated with a slurry, it is most advantageous if the slurry has a viscosity that will allow the slurry to flow into depressions or cavities in the patterned surface. Thus, slurries having low viscosity are quite advantageous. One way of achieving this is through the use of viscosity modifiers, such as amorphous silica particles having an average surface area of 50 $m^2/g$, and average particle size of 40 millimicrometers, commercially available from Degussa Corp, Ridgefield Park, NJ, under the trade designation OX-50, as disclosed in assignee's pending application Ser. No. 07/992,137, filed Dec. 17, 1992. The production tool can be a belt, a sheet, a continuous sheet or web, a coating roll such as a rotogravure roll, a sleeve mounted on a coating roll, or die. The production tool can be composed of metal, (e.g., nickel), metal alloys, or plastic. The metal production tool can be fabricated by any conventional technique such as engraving, hobbing, electroforming, diamond turning, and the like. One preferred technique for fabricating a metal production tool is by diamond turning.

A thermoplastic tool can be replicated off a metal master tool. The master tool will have the inverse pattern desired for the production tool. The master tool can be made in the same manner as the production tool. The master tool is preferably made from metal, e.g., nickel and is diamond turned. The thermoplastic sheet material can be heated and optionally along with the master tool such that the thermoplastic material is embossed with the master tool pattern by pressing the two together. The thermoplastic material can also be extruded or cast onto the master tool and then pressed. In both cases, the thermoplastic material is cooled below its glass transition temperature to produce the production tool. Examples of preferred thermoplastic production tool materials include polyester, polycarbonate, polyvinyl chloride, polypropylene, polyethylene and combinations thereof. If a thermoplastic production tool is utilized, then care must be taken not to generate excessive heat that may distort the tool.

The production tool may also contain a release coating to permit easier release of the abrasive article from the production tool. Examples of such release coatings for metals include hard carbide, nitride or boride coatings. Examples of release coatings for thermoplastics include silicones and fluorochemicals.

Referring specifically to FIG. 2, there is illustrated, in cross section, enlarged, an abrasive article embodiment 20 comprising a plurality of precisely shaped abrasive composites 22 separated by boundary 25. The boundary or boundaries associated with the composite shape result in one abrasive composite being separated to some degree from another adjacent abrasive composite. To form an individual abrasive composite, a portion of the boundaries forming the shape of the abrasive composite must be separated from one another. Note that in the article illustrated in FIG. 2, the base or a portion of the abrasive composite closest to the backing can abutt with its neighboring abrasive composite. (Note that "neighboring" does not necessarily mean "adjacent".) Abrasive composites 22 comprise a plurality of abrasive particles 24 that are dispersed in a binder 23 optionally containing grinding aid particles 26. It is also within the scope of this invention to have a combination of abrasive composites bonded to a backing in which some of the abrasive composites abutt, while other abrasive composites have open spaces between them.

One preferred method of making a lapping coated abrasive such as illustrated in FIG. 2 is to first coat a coatable composition (sometimes referred to herein as a slurry) within the invention onto at least one side of a backing, applied using one of the previously mentioned suitable techniques. The preferred backing is a polymeric film, such as polyester film that contains an ethylene acrylic acid copolymer primer. Second, the slurry-coated backing is contacted with the outer surface of a patterned production tool. The slurry wets the patterned surface to form an intermediate article. Third, the slurry is subjected to radiation, preferably in the UV and/or visible spectrum ranging from about 300 nanometers to about 1000 nanometers, preferably from about 300 to about 400 nanometers, and other optional energy sources, as previously described which at least partially cures or gels the resin in the slurry before the intermediate article is removed from the outer surface of the production tool. Fourth, the intermediate article is removed from the production tool. The four steps are preferably carried out continuously.

Figure 3:
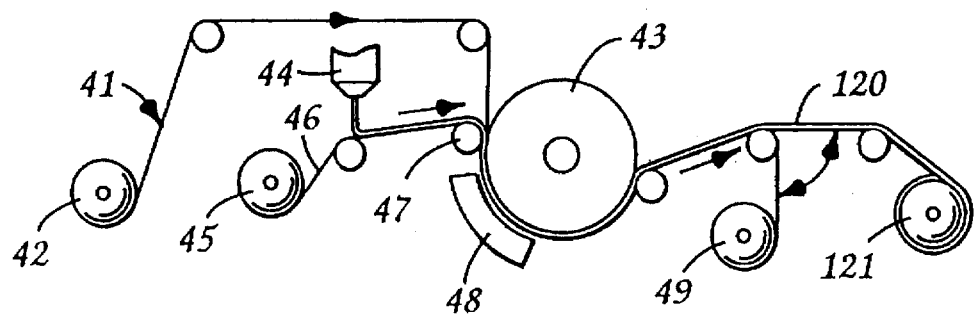
FIG. 3 is a schematic of a process of making the abrasive article of FIG. 2.
Figure 4:
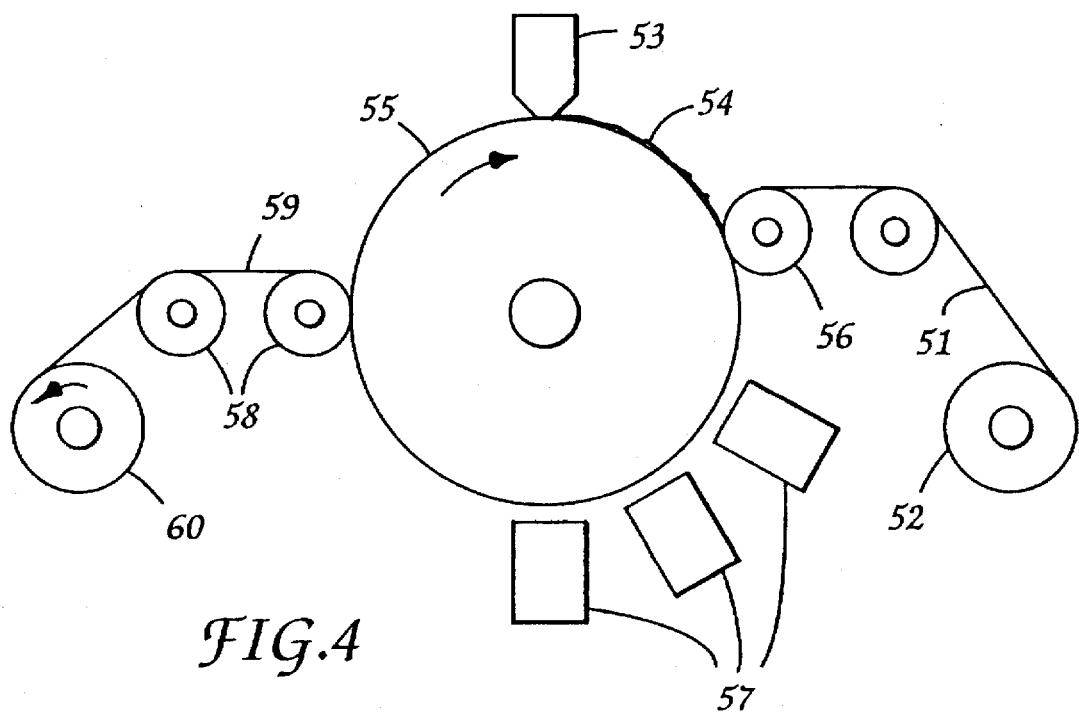
FIG. 4 is a schematic of another process of making the abrasive article of FIG. 2.

Alternatively, the slurry may be first applied to the production tool in the methods illustrated in FIGS. 3 and 4. In FIG. 3, backing 41 leaves an unwind station 42 and at the same time the production tool 46 leaves an unwind station 45. Production tool 46 is coated with a slurry by means of coating station 44. It is possible to heat the slurry and/or subject the slurry to ultrasonics prior to coating to lower the viscosity. The coating station can be any conventional coating means such as drop die coater, knife coater, curtain coater, die coater, or vacuum die coater. During coating the formation of air bubbles should be minimized. The preferred coating technique is a vacuum fluid bearing die, such as disclosed in U.S. Pat. Nos. 3,594,865, 4,959,265, and 5,077,870, all incorporated herein by reference. After the production tool is coated, the backing and the slurry are brought into contact by any means such that the slurry wets the front surface of the backing. In FIG. 3, the slurry is brought into contact with the backing by means of contact nip roll 47. Next, contact nip roll 47 also forces the resulting construction against support drum 43. A source of energy 48 providing radiation, preferably in the UV and/or visible spectrum ranging from about 300 nanometers to about 1000 nanometers, preferably about 300 to about 400 nanometers, and other optional energy sources, transmits a sufficient amount of energy into the slurry to at least partially cure the binder precursor. The term "partial cure" means that the binder precursor is polymerized to such a state that the slurry does not flow from an inverted test tube. The binder precursor can be fully cured once it is removed from the production tool by an appropriate energy source. Following this, the production tool is rewound on mandrel 49 so that the production tool can be reused again. Additionally, abrasive article 120 is wound on mandrel 121. If the binder precursor is partially cured, the binder precursor can then be more fully cured by exposure to an energy source, preferably a combination of UV and/or visible radiation and thermal energy.

The inventive coatable compositions can be coated onto the backing and not into the cavities of the production tool. The slurry coated backing is then brought into contact with the production tool such that the slurry flows into the cavities of the production tool. The remaining steps to make the abrasive article are the same as detailed above.

Another method is illustrated in FIG. 4. Backing 51 leaves an unwind station 52 and the slurry 54 is coated into the cavities of the production tool 55 by means of the coating station 53. The slurry can be coated onto the tool by any one of many techniques previously mentioned. Again, it is possible to heat the slurry and/or subject the slurry to ultrasonics prior to coating to lower the viscosity. During coating the formation of air bubbles should be minimized. Then, the backing and the production tool containing the abrasive slurry are brought into contact by a nip roll 56 such that the slurry wets the front surface of the backing. Next, the binder precursor in the slurry is at least partially cured by exposure to an energy source 57, preferably providing radiation in at least some portion of the UV and/or visible spectrum ranging from about 300 nanometers to about 1000 nanometers, and other optional energy sources. After this at least partial cure, the slurry is converted to an abrasive composite 59 that is bonded or adhered to the backing. The resulting abrasive article is removed from the production tool by means of nip rolls 58 and wound onto a rewind station 60. In this method the preferred backing is polyester film.

Regarding this latter method, the slurry can be coated directly onto the front surface of the backing. The slurry coated backing is then brought into contact with the production tool such that the slurry wets into the cavities of the production tool. The remaining steps to make the abrasive article are the same as detailed above.

In methods employing a production tool, the production tool may be coated with a release agent, such as a silicone material, to enhance the release of the intermediate article from the patterned tool.

Because the pattern of the production tool imparts a pattern to the abrasive articles of the invention, these methods are particularly useful in making "structured" abrasive articles. A structured abrasive article is an abrasive article wherein composites, comprising abrasive particles distributed in a binder, have a predetermined shape, and are disposed in a predetermined array on a backing. The slurry is preferably coated onto a production tool having a pyramidal or other type pattern such that the slurry fills the tool. The pyramids may be placed such that their bases are butted up against one another. The width of the pyramid base preferably ranges from about 100 micrometers to about 1000 micrometers, with the pyramid height having the same range, although the base width and height may be the same or different within a pyramid or from pyramid to pyramid. One preferred pattern is illustrated in FIG. 1 of the Pieper et al. patent.

Additional Methods of Making Coated Abrasives

The present invention also relates to methods of manufacturing conventional coated abrasive articles incorporating the reactive diluents within general formulas (I)–(V).

In one preferred method in accordance with the invention, a slurry comprising an addition polymerizable resin, reactive diluent within general formulas (I)–(V), abrasive particles, and optional ingredients such as fillers, coupling agents, and the like, is coated onto a backing. The backing may be first saturated with a saturant coating precursor by any conventional technique such as dip coating or roll coating, after which the saturant coating precursor is partially cured ("precure"). After the saturant coating precursor is at least partially cured, a make coating precursor may be applied by any conventional technique such as roll coating, die coating or knife coating. Abrasive particles are then applied to the coated backing by a method such as drop coating, electrostatic coating, and the like. The make coating precursor is then exposed to conditions sufficient to at least partially cure or gel the polymerizable moieties in the slurry.

A size coating precursor may then be applied over the abrasive grains by any of the above-mentioned conventional techniques, and subjected to conditions to effect a partial cure.

One or more supersize coating precursors may be applied over the partially cured size coating by any conventional technique. Each of the coatings may be fully cured, partially cured or dried after it is applied. After the last coating precursor is applied, and if necessary, any remaining partially cured or dried coatings are fully cured. In these methods, the optional size and supersize coatings may comprise binder materials that are commonly utilized in the coated abrasive art (for example resole phenolic resins), or may also comprise slurries or binder precursor compositions including a reactive diluent within general formulas (I)–(V).

Some of the abrasive articles produced and used in the Examples below were made according to the General Procedure for Preparing the Abrasive Article, and the abrasive articles were tested according to the test procedures described below.

TEST METHODS

KNOOP HARDNESS INDENTATION TEST

This indentation hardness determination of organic/polymeric coatings is described in ASTM D 1474-85 (Method A). Coatings of approximately 15 mils were applied to glass microscope slides. Subsequently, the coatings were dried and/or cured by an energy source. The method consisted of applying a 100 gram load to the surface of a coating by means of a pyramidal shaped diamond having specified face angles, and converting the length measurement of the resulting permanent indentation to the Knoop Hardness Number. Typical KHN values for coatings of abrasive binders are known to generally range from 20 to 50. A Tukon Hardness Tester, Model 200, available from Wilson Instruments of Binghampton, NY, was used to determine the KHN.

ABRASIVE TEST PROCEDURE 1 (TP1)

The coated abrasive article was converted into 7.6 cm by 356 cm endless abrasive belts. Two belts from each example were tested on a wood sander. A pre-weighed fir workpiece approximately 1.9 cm by 30.5 cm by 76.2 cm was mounted in a holder, positioned horizontally, with the 1.9 cm by 30.5 cm face confronting a horizontally positioned backup plate with a graphite pad over which the coated abrasive belt ran. The workpiece was urged against the belt with a load of 4.5 kilograms (kg) as the belt was driven at about 1,000 meters/min. After five minutes of sanding time had elapsed, the workpiece was removed and reweighed, the amount of wood removed calculated by subtracting the weight after abrading from the original weight. Then, a new, pre-weighed workpiece was mounted on the equipment. The total cut is a measure of the total amount of wood removed throughout the test after twenty-five minutes (five workpieces five minutes each).

ABRASIVE TEST PROCEDURE 2 (TP2)

This test procedure is identical to Test Procedure 1 (TP1) except that pine workpieces were sanded.

ABRASIVE TEST PROCEDURE 3 (TP3)

The coated abrasive article of each of the following examples was converted into 7.6 cm by 335 cm endless abrasive belts. Two belts from each example were tested on a constant load surface grinder. A pre-weighed, 1018 steel workpiece approximately 2.5 cm by 5 cm by 18 cm was mounted in a holder, positioned vertically, with the 2.5 cm by 18 cm face confronting an approximately 36 cm diameter 60 Shore A durometer serrated rubber contact wheel having one to one land to groove over which entrained the coated abrasive belt. The workpiece was then reciprocated vertically through an 18 cm path at the rate of 20 cycles per minute, while a spring-loaded plunger urged the workpiece against the belt with a load of 5.9 kg as the belt was driven at about 2,050 meters/min. After one minute of grinding time had elapsed, the workpiece holder assembly was removed and reweighed, and the amount of stock removed was calculated by subtracting the weight after abrading from the original weight. Then a new, pre-weighed workpiece and holder were mounted on the equipment. The experimental error on this test was about 10%. The total cut is a measure of the total amount of 1018 steel removed throughout the test. The test was deemed ended when the amount of final cut was less than one third the amount of initial cut of test control belt for a one minute time interval.

ABRASIVE TEST PROCEDURE 4 (TP4)

This Test Procedure 4 was designed to measure the time it took for the abrasive grain to shell from a coated abrasive disc. The test equipment included a 17.8 cm diameter test coated abrasive disc with a 2.2 cm mounting hole attached to a 16.5 cm diameter 1.57 mm thick hard phenolic backup pad which was in turn mounted on a 15.2 cm diameter steel flange. The test disc so supported was rotated counterclockwise at 3550 rpm. The 1.8 mm peripheral edge of a 25 cm diameter 4130 steel disc shaped workpiece deployed 18.5 cm from a position normal to the abrasive disc and rotated counter clockwise at 2 rpm, was placed into contact with the abrasive face of the abrasive disc under a load of 2.9 kg. The test endpoint was 8 minutes or when the disc began to shell, i.e., a substantial portion of its abrasive grain flew off of the discs, whichever occurred first. At the end of the test, the workpiece was weighed to determine the amount of metal cut (abraded) from the workpiece. The values listed in the Tables are measured as a percent of the Comparative Example.

ABRASIVE TEST PROCEDURE 5 (TP5)

Coated abrasive discs having a diameter of 17.8 cm, with a 2.2 cm diameter center hole and thickness of 0.76 mm were installed on a slide action testing machine. The discs were first conventionally flexed to controllably break the hard bonding resins, mounted on a beveled aluminum back-up pad, and used to grind the face of 2.5 cm by 18 cm 1018 mild steel workpiece. The disc was driven at 5,500 rpm while the portion of the disc overlaying the beveled edge of the back-up pad contacted the workpiece at 5.91 kg pressure, generating a disc wear path of about 140 cm$^2$. Each disc was used to grind a separate workpiece for one minute each, for a total time of 12 minutes each, or for sufficient one minute time segments until no more than 5 grams of metal were removed in any one minute of grinding.

Dynamic Mechanical Analysis

Dynamic mechanical analysis testing was performed using an instrument known under the trade designation "Rheometrics RSA II Solids Analyzer", commercially available from Rheometrics Company, Piscataway, NJ. A rectangular cell which contained the sample to be tested was used in each case. The samples in each case consisted of a glass fiber cloth (available from TA Instruments, New Castle, DE) impregnated with the composition to be tested. The compositions were then cured by a double pass under a 300 watt "D" type ultraviolet source. The cured composition/fiber composites were then loaded into a film-fiber fixture and temperature sweep tests were performed at a stepped 5° C./minute. A 6.28 Hz frequency was used for all measurements.

| MATERIALS DESCRIPTION |
| --- |
| Di(acryloyloxyethyl)phthalate (DAP) |
| (Acryloyloxyethyl)salicylate (SEA) |
| 2,6-Di(acryloyloxymethyl)-p-cresol acrylate (CTA) |
| 2-(Acryloyloxyethoxy)phenol acrylate (PPEDA) |
| N,N'-Di(acryloyloxyethyl)-N,N'-dimethyl phthalamide (DAMP) |
| N,N'-Di(acryloyloxyethyl)-N,N'-diethyl phthalamide (DAEP) |
| N,N'-Di(acryloyloxyethyl)-N,N'-dipropyl phthalamide (DAPP) |
| Acryloyloxyethyl-N-methyl anilide (PMMA) |
| (Acryloyloxyethyl)benzoate (BEA) |
| Phenoxyethyl acrylate (PEA) commercial diluent |
| Benzyl acrylate (BA) commercial diluent |
| N-(Acryloyloxyethyl)tetrahydrophthalimide (4HPIA) |
| N-(Acryloyloxyethyl)hexahydrophthalimide (6HPIA) |
| N-(Acryloyloxyethyl)methylnadimide (MNIA) |

| MATERIALS DESCRIPTION —continued |
| --- |
| N-(Acryloyloxypropyl)hexahydrophthalimide (6HPIPA) |
| N-(Acryloyloxyethylethoxy)hexahydrophthalimide (6HPIEEA) |
| N-[2,3-Di(acryloyloxy)propyl]tetrahydrophthalimide (4HPIDA) |
| N-[2,3-Di(acryloyloxy)propyl]hexahydrophthalimide (6HPIDA) |
| N-(Acryloyloxyethyl)pyrrolidone (PYA) |
| 5-Acryloyloxymethyl-oxazolidin-2-one (OXA) |
| 5-(Acryloyloxethyl)-4-methylthiazole (MTA) |
| 2-(Acryloyloxethyl)furoate (FEA) |
| 2-[N-(Acryloyloxyethyl)-N-methyl]furancarboxamide (FAEA) |
| 2-(Acryloyloxyethyl)thenoate (ThEA) |
| 2-[N-(Acryloyloxyethyl)-N-methyl]thiophenecarboxamide (ThMAA) |
| 2-(N-(Acryloyloxyethyl)-N-ethyl]thiophenecarboxamide (ThEAA) |
| 2-[N-(Acryloyloxyethyl)-N-propyl]thiophenecarboxamide (ThPAA) |
| 2-[N-Di(acryloyloxyethyl)]thiophenecarboxamide (ThDEAA) (OXDA) |
| (2-oxo-11,3-dioxolan-4-yl)methyl acrylate (GCA) |
| 2-[N-Di(acryloyloxyethyl)]furancarboxamide (FDEAA) |
| N-2-(Acryloyloxyethyl)morpholine (AMA) |
| N-(2-Acryloyloxethyl)-N'-(acryloyl)piperazine (PEAA) |
| N-Acryloylmorpholine (AMORPH) |
| N-(2-Acryloyloxyethyl)ethyleneurea (RDUA) |
| 5-(Acryloyloxymethyl)-2,2-dimethyldioxolane (KDM) |
| (2-Ethyl-2-methyl-1,3-dioxolan-4-yl)methyl acrylate (KEM) |
| 5-(Acryloyloxymethyl)-2,2-cyclopentyldioxolane (KCP) |
| 5-(Acryloyloxymethyl)-2,2-dimethyl-5-ethyl-1,3-dioxane (KDME) |
| 5-(Acryloyloxymethyl)-2-ethyl-2-methyl-5-ethyl-1,3-dioxane (KEEM) |
| 2-(2-Acryloyloxyethyl)-N-(acryloyl)piperidine (AAP) |
| RP1 — a resole phenolic resin (74% solids in water/2-ethoxy ethanol) |
| IO — red iron oxide |
| CACO — calcium carbonate |
| CRY — cryolite (trisodium hexafluoroaluminate) |
| TATHEIC — triacrylate of tris(hydroxyethyl) isocyanurate |
| TMPTA — trimethylolpropane triacrylate |
| PH1 — 2,2-dimethoxy-1-2-diphenyl-1-ethanone, commercially available from Ciba-Geigy Corporation, Hawthorne, NY, under the trade designation IRGACURE 651 |
| GUAM — an aminoplast resin having pendant acrylate functional groups, prepared in a manner similar to that described in U.S. Pat. No. 5,055,113, Preparation 5 |
| AMP — an aminoplast resin having pendant acrylate functional groups, prepared in a manner similar to that described in U.S. Pat. No. 4,903,440, Preparation 4 |
| NPGDA — neopentylglycol diacrylate |
| PETA — pentaerythritol triacrylate |
| T4EGDA — tetraethyleneglycol diacrylate (commercially available from Sartomer Company, Exton, PA, under the trade designation SR-268); |
| BAM — an aminoplast resin having pendant acrylate functional groups, prepared in a manner similar to that described in U.S. Pat. No. 4,903,440, Preparation 2 |
| HP — a mixture of 15 parts water and 85 parts 2-methoxy propanol, available under the trade designation "Polysolve PM" from Olin Chemical, Stamford, CT. |

EXAMPLES

The following non-limiting examples will further illustrate the articles and methods of the present invention. All parts and percentages are based upon weight unless specified differently. "ASTM" refers to American Society of Testing and Materials; "IR" refers to the well known infrared spectroscopy analytical method; "$^{13}$C NMR" refers to the well known carbon 13 nuclear magnetic resonance analytical method; "g" refers to grams; "ml" refers to milliliters; "gsm" refers to grams per square meter; "aq." refers to aqueous; "mol." refers to moles; "mmHg" refers to millimeters mercury; "Pa" refers to Pascals; and "kPa" refers to kiloPascals.

Example 1.

Acryloyloxyethylsalicylate (SEA)

To a two liter, three necked, round bottomed flask equipped with a thermometer, Dean-Stark trap, water cooled condenser, paddle stirrer and heating mantle was added 498 g (2.73 mol.) of hydroxyethylsalicylate, 1000 ml of benzene, 1.0 g of phenothiazine, 1.0 g of 4-methoxyphenol, 238 g (3.30 mol.) of acrylic acid and 10.0 g of methanesulfonic acid. Stirring was started. The reaction was heated to reflux. After 12 hours, the theoretical amount of water was collected. The reaction contents were cooled to room temperature, water was added and the reaction neutralized with NaHCO$_3$. The organic layer was washed twice more with an equal quantity of water, then dried over Na$_2$SO$_4$ and filtered. The benzene was removed by rotoevaporation. The crude product was distilled at reduced pressure, to recover 530 g (83%) of an off white liquid, b.p. 135° C. at 0.20 mmHg (26.7 Pa). The liquid was confirmed by $^{13}$C NMR to be the desired product.

Example 2.

2,6-Di(acryloyloxymethyl)acryloyloxy-p-cresol (CTA)

A two liter, three necked flask was equipped with an overhead stirrer, nitrogen atmosphere and an addition funnel. Next, the flask was charged with 100 g of 2,6-bis (hydroxymethyl)-p-cresol (0.59 mol.), 800 ml of tetrahydrofuran, 180 g of triethylamine (1.78 mol.) 1.2 g of 4-dimethylaminopyridine and 1 g of phenothiazine. The reaction was cooled with an ice bath and 161 g of acryloyl chloride (1.78 mol.) was added slowly over 1.5 hour. Next, the reaction was warmed to room temperature and stirred for 3 hours. The triethylamine hydrochloride salt was removed by filtration. The remaining mother liquor was evaporated with a rotoevaporator to yield a light brown liquid. The liquid was dissolved in ethyl acetate and washed with HCl(10%), NaCl(aq.), NH$_4$OH(10%), NaCl(aq.) and dried over MgSO$_4$. The ethyl acetate was removed with a rotoevaporator to yield 85 g (44%) of a water white liquid. The liquid became a white semi-solid upon standing. The product was confirmed by IR and $^{13}$C NMR.

Example 3.

2-(Acryloyloxyethoxy)acryloyloxyphenol (PPEDA)

A 500-ml, two necked flask was equipped with a magnetic stirring bar, nitrogen atmosphere and an addition funnel. The flask was charged with 25 g of 2-(2-hydroxyethoxy)phenol (0.16 mol.), 33 g of triethylamine (0.32 mol.), 250 ml of tetrahydrofuran and 1 g of phenothiazine. Next, 30 g of acryloyl chloride (0.18 mol.) was slowly added to the reaction over 1 hour via the addition funnel. The triethylamine hydrochloride salt was removed by filtration and the mother liquor was evaporated with a rotoevaporator. The remaining liquid was dissolved in chloroform and washed with NaCl(aq.), NH$_4$OH(10%), NaCl(aq.) and dried over MgSO$_4$. The chloroform was removed with a rotoevaporator to yield 26 g (62%) of a reddish brown liquid. The product was confirmed by IR.

Example 4.

N,N'-Di(acryloyloxyethyl)-N,N'-dimethylphthalamide (DAMP)

A one liter, three necked flask was equipped with an overhead stirrer, nitrogen atmosphere and an addition funnel. The flask was charged with 148 g of 2-(methylamino) ethanol (1.97 mol.) and 600 ml of dichloromethane. The flask was cooled with an ice bath. Next, 100 g of phthaloyl chloride (0.49 mol.) was slowly added via the addition funnel over 5.5 hours. The dichloromethane was washed with NaCl(aq.). Next, the NaCl(aq.) layer was extracted with dichloromethane and the two dichloromethane layers were combined. The organic layer was evaporated with a rotoevaporator to yield 76 g (55%) of phthalamide diol.

A one liter, three necked flask was equipped with overhead stirrer, nitrogen atmosphere and an addition funnel. The flask was charged with 100 g of N,N'-di(hydroxyethyl) -N,N'-dimethyl phthalamide (0.36 mol.), 67.8 g of triethylamine (0.72 mol.), 500 ml of tetrahydrofuran and 2 g of phenothiazine. Next, 68 g of acryloyl chloride (0.75 mol.) was slowly added to the flask over one hour. The reaction was stirred for an additional hour. The triethylamine hydrochloride salt was removed by filtration and the remaining mother liquor was evaporated with a rotoevaporator to yield a light brown liquid. The liquid was dissolved in chloroform and washed with NaCl(aq.), NH$_4$OH(10%), NaCl(aq.) and dried over MgSO$_4$. The chloroform was removed with a rotoevaporator to yield 60 g (43%) of a light brown liquid. The product was confirmed by IR and $^{13}$C NMR.

Example 5.

Di(acryloyloxyethyl)phthalate (DAP)

A five liter, three necked flask was equipped with a overhead stirrer, nitrogen atmosphere and addition funnel. The flask was charged with 636 g of 2-hydroxyethylacrylate (5.47 mol.), 547 g of triethylamine (5.41 mol.), 6 g of phenothiazine, 5 g of 4-dimethylaminopyridine and 3000 ml of tetrahydrofuran. The reaction was cooled to 17° C. with a water bath. Next, 563 g of phthaloyl chloride (2.75 mol.) was slowly added over 2.5 hours via the addition funnel. The reaction was stirred an additional 8 hours at room temperature. The triethylamine hydrochloride salt was removed by filtration and the mother liquor evaporated by rotoevaporation to yield an amber colored liquid. The liquid was placed under vacuum (15 mmHg, 2 kPa) and heated to 100° C. for one hour. The resulting liquid was collected to yield 995 g (99%) of the desired product. The product was confirmed by IR and $^{13}$C NMR. The preparation of di(acryloyloxyethyl) phthalate from phthalic anhydride and 2-hydroxyethylacrylate was reported in U.S. Pat. No. 3,336, 418.

Example 6.

N-(Acryloyloxyethoxyethyl)hexahydrophthalimide (6HPIEEA)

A 500-ml, two necked flask was equipped with a magnetic stirring bar, heating mantle and condenser. The flask was charged with 51 g of 2-(aminoethoxy)ethanol (0.49 mol.) and 250 ml of ethanol. Next, 75 g of hexahydrophthalic anhydride (0.49 mol.) was slowly added to the flask. After the addition was complete the reaction was refluxed for 12 hours. The IR spectrum indicated the reaction was complete. The ethanol was removed with a rotoevaporator to yield 113 g (96%) of N-(2-hydroxyethoxyethyl) hexahydrophthalimide.

A one liter, three necked flask was equipped with overhead stirrer, nitrogen atmosphere and an addition funnel. The flask was charged with 100 g of N-(2-hydroxyethoxyethyl)hexahydrophthalimide (0.41 mol.), 42 g of triethylamine (0.41 mol.), 1 g of phenothiazine and 400 ml of acetone. Next, 38 g of acryloyl chloride (0.41 mol.) was added slowly to the flask via the addition funnel over 45 minutes. The reaction was stirred for an additional 12 hours. The triethylamine hydrochloride salt was removed by filtration and the remaining mother liquor was evaporated with a rotoevaporator. The resulting red-orange liquid was dissolved in chloroform and extracted with HCl(10%), NaCl (aq.), NH$_4$OH(10%), NaCl(aq.) and dried over MgSO$_4$. The chloroform was removed with a rotoevaporator to yield 72 g (59%) of an orange-red liquid. The product was confirmed by IR and $^{13}$C NMR.

Example 7.

N-(2,3-Di(acryloyloxy)propyl)hexahydrophthalimlde (6HPIDA)

A 500-ml, two necked flask was equipped with a magnetic stirring bar, heating mantle and condenser. The flask was charged with 46 g of 3-amino-1,2-propanediol (0.50 mol.) and 300 ml of ethanol. Next, 77 g of hexahydrophthalic anhydride (0.50 mol.) was slowly added to the flask after which the reaction was refluxed for 12 hours. The imide formation was confirmed by IR. The ethanol was removed by a rotoevaporator to yield 92 g (81%) of the N-(2,3-dihydroxypropyl)hexahydrophthalimide.

A one liter, three necked flask was equipped with overhead stirrer, nitrogen atmosphere and an addition funnel. The flask was charged with 70 g of N-(2,3-dihydroxypropyl)hexahydrophthalimide (0.34 mol.), 69 g of triethylamine (0.34 mol.), 2 g of 4-dimethylaminopyridine, 500 ml of acetone and 0.5 g of phenothiazine. Next, 62 g of acryloyl chloride (0.68 mol.) was added over 1.5 hour via the addition funnel. The reaction was stirred an additional 12 hours at room temperature (about 20° C.). The triethylamine hydrochloride salt was removed by filtration and the mother liquor was evaporated with a rotoevaporator. The resulting liquid was dissolved in chloroform and washed with NaCl (aq.), NH$_4$OH(10%), NaCl(aq.) and dried over MgSO$_4$. The chloroform was removed with a rotoevaporator to yield 80 g (90%) of an orange-red liquid. The product was shown by IR and $^{13}$C NMR to be 85% N-[2,3-di(acryloyloxy)propyl]hexahydrophthalimide and 15% N-[(2-hydroxy-3-acryloyloxy)propyl]hexahydrophthalimide.

Example 8.

(2-Ethyl-2-methyl-1,3-dioxolan-4-yl)methyl Acrylate (KEM)

To a two liter, three necked, round bottomed flask equipped with a thermometer, paddle stirrer, Dean-Stark trap, water cooled condenser and heating mantle was added 400 g (4.34 mol.) of glycerol, 500 ml of methyl ethyl ketone, 500 ml cyclohexane and 8.0 g of p-toluenesulfonic acid hydrate. The reaction contents were stirred and heated to reflux. After 24 hours, the theoretical amount of water was collected. The reaction contents were cooled to room temperature, while stirring. 8 g of sodium acetate were added and the reaction product distilled to purity. 563 g (89%) of pure product, b.p. 83° C. at 3.7 mmHg (1.73 kPa), were obtained. The compound was identified by IR.

To a two liter, three necked, round bottomed flask equipped with a thermometer, paddle stirrer, pressure equalizing dropping funnel and brine bath was added 146.2 g (1 mol.) of the above alcohol, followed by 800 ml of tetrahydrofuran, 104 g (1.03 mol.) of triethylamine and 0.5 g of phenothiazine. Stirring was begun and the reaction contents chilled. To the dropping funnel was added 90.5 g (1.0 mol.) of acryloyl chloride. This was added to the reaction flask over one hour, allowing the temperature to rise to 10° C. The reaction was allowed to stir overnight at room temperature and filtered. The triethylamine was rinsed with a little dioxane and the solution allowed to stand over Na$_2$CO$_3$ and Na$_2$SO$_4$. The yellow solution was filtered and concentrated on a rotoevaporator. Distillation at reduced pressure gave 168 g (84%) of a colorless liquid, b.p. 98°–100° C. at 0.20 mmHg (26.7 Pa). The compound was identified by IR.

Example 9.

(2-Oxo-1,3-dioxolan-4-yl)methyl Acrylate (GCA)

Following a modified example given in U.S. Pat. No. 2,915,529, to a one liter, three necked flask equipped with a paddle stirrer, water cooled condenser, thermometer and heating mantle was added 368 g (4 mol.) of glycerol, 702 g (8 mol.) of ethylene carbonate and 0.11 g of NaHCO$_3$. The contents of the flask were heated to 130° C., while stirring, and held at this temperature for 45 minutes. The reaction contents were cooled to 100° C. 500 g of this solution were transferred to a distillation apparatus. The solution was distilled under reduced pressure. A forerun was collected up to 140° C. at 13 mmHg (1.73 kPa) and discarded. The product, a colorless liquid, was collected from 150°–152° C. at 0.1 mmHg (13.3 Pa). The yield was 80%. The compound was confirmed to be the glycerol carbonate by $^{13}$C NMR.

Following a similar preparation as described by D'Alelio and Huemmer (J. Poly. Sci., 5, 1967, pp. 307–321), to a two liter, three necked, round bottomed flask equipped with a paddle stirrer and thermometer, was added 87 g (0.74 mol.) of glycerol carbonate, followed by 1000 ml of benzene, 100 ml dioxane and 0.95 g of BHT. A drying tube and a nitrogen line were attached to the flask. Stirring was begun and the heterogeneous mixture was cooled to 0° C. with a brine bath. Two addition funnels were charged as follows: to the first was added (0.74 mol.) of triethylamine; to the second was added a solution of 100 ml of benzene and 60 g (0.66 mol.) of acryloyl chloride. Two drops of acryloyl chloride solution were added for every one drop of triethylamine. The addition took place over a period of two hours. The reaction contents were filtered through diatomaceous earth filtering media and the solution was washed with cold 5% HCl, followed by four 200 ml portions of water. 0.3 g of tert-butanol was added and the solution was dried over MgSO$_4$. The solution was filtered to remove the drying agent and allowed to stand over a mixture of NaHCO$_3$ and Na$_2$SO$_4$ for two days. The solution was filtered, transferred to a one liter, round bottomed flask and placed on a rotoevaporator. Without heat being applied, a vacuum of approximately 5 mmHg (667 Pa) was applied and the solvent was removed as completely as possible. 52 g (42%) of a light yellow liquid was recovered. $^{13}$C NMR identified the liquid to contain 86%, by weight, of the desired compound, the balance being benzene and dioxane.

Example 10.

N-(Acryloyloxyethyl)pyrrolidone (PYA)

Following a modified example in U.S. Pat. No. 2,882,262, a one liter three necked flask was equipped with overhead stirrer, Dean-Stark trap, condenser and heating mantle. The flask was charged with 129 g of 2-(hydroxyethyl) pyrrolidone (1 mol.), 80 g of acrylic acid (1.1 mol.), 400 ml of toluene, 7 g of p-toluenesulfonic acid and 2 g of 4-methoxyphenol. The reaction was refluxed for 24 hours over which 1 mol. of water was collected. Next, the toluene was removed by simple distillation. The remaining liquid was vacuum distilled and a 73 g (40%) fraction was collected at 125°–130° C. at 0.8 mmHg (107 Pa). The product was confirmed by IR and $^{13}$C NMR.

Example 11.

2-(N-Acryloyloxyethyl)-N-methylfuranamide (FAEA)

A one liter, three necked flask was equipped with overhead stirrer, nitrogen atmosphere and an addition funnel. The flask was charged with 115 g of 2-(methylamino) ethanol (1.53 mol.) and 500 ml of dichloromethane. The reaction flask was cooled with an ice bath. Next, 100 g of furoyl chloride (0.77 mol.) was slowly added via the addition funnel over 2.5 hours. The dichloromethane was washed with NaCl(aq.). Next, the NaCl(aq.) layer was extracted with dichloromethane and the two dichloromethane layers were combined and dried over $MgSO_4$. The dichloromethane was removed with a rotoevaporator to yield 77 g (44%) of N-(2-hydroxyethyl)-N-methylfuranamide.

A one liter, three necked flask was equipped with overhead stirrer, nitrogen atmosphere and an addition funnel. The flask was charged with 75 g of N-(2-hydroxyethyl)-N-methylfuranamide (0.44 mol.), 50 g of triethylamine (0.44 mol.), 500 ml of tetrahydrofuran and 2 g of phenothiazine. Next, 40 g of acryloyl chloride (0.44 mol.) was slowly added to the reaction over 1.5 hour via the addition funnel. The reaction was stirred at room temperature (about 25° C.) for 1 hour. The triethylamine hydrochloride salt was removed by filtration and the mother liquor evaporated with a rotoevaporator. The remaining liquid was dissolved in chloroform and washed with NaCl(aq.), $NH_4OH$(10%), NaCl(aq.) and dried over $MgSO_4$. The chloroform was removed with a rotoevaporator to yield 86 g (87%) of a light brown liquid. The compound was confirmed by IR and $^{13}C$ NMR.

Example 12.

2-(Acryloyloxyethyl)thenoate (ThEA)

A five liter, three necked flask was equipped with overhead stirrer, nitrogen atmosphere and an addition funnel. The flask was charged with 238 g of 2-hydroxyethylacrylate (2.04 mol.), 207 g of triethylamine (2.04 mol.), 1500 ml of tetrahydrofuran and 10 g of phenothiazine. Next, 300 g of 2-thiophenecarbonylchloride (2.04 mol.) was slowly added to the reaction over 3 hours via the addition funnel. The reaction was stirred 12 hours at room temperature. The triethylamine hydrochloride salt was removed by filtration and the mother liquor evaporated with a rotoevaporator. The remaining liquid was distilled and 337 g (73%) was collected at 120°–123° C. at 5 mmHg (667 Pa). The compound was confirmed by IR and $^{13}C$ NMR.

Example 13.

2-(Acryloyloxyethyl)-3-methylthiazole (MTA)

A one liter, three necked flask was equipped with overhead stirrer, nitrogen atmosphere and an addition funnel. The flask was charged with 100 g of 2-(2-hydroxyethyl)-3-methylthiazole (0.70 mol.), 71 g of triethylamine (0.70 mol.), 500 g of chloroform and 3 g of phenothiazine. Next, 63 g of acryloyl chloride (0.70 mol.) was slowly added to the reaction over 1.5 hour via the addition funnel. The reaction was stirred for 2 hours at room temperature. The reaction mixture was extracted with NaCl(aq.), $NH_4OH$(10%), NaCl (aq.) and dried over $MgSO_4$. The chloroform was evaporated with a rotoevaporator to yield 113 g (82%) of a dark brown liquid. The compound was confirmed by IR and $^{13}C$ NMR.

Example 14.

2-[N,N'-Di(acryloyloxyethyl)]thiopheneamide (ThDEAA)

A one liter, three necked flask was equipped with overhead stirrer, nitrogen atmosphere and an addition funnel. The flask was charged with 143 g of diethanolamine (0.68 mol.) and 500 ml of dichloromethane. The reaction flask was cooled with an ice bath. Next, 100 g of 2-thiophenecarbonylchloride (0.68 mol.) was slowly added to the reaction over 4 hours via the addition funnel. The reaction was stirred for 12 hours at room temperature. The dichloromethane reaction mixture was washed with NaCl (aq.). Next, the NaCl(aq.) layer was extracted with dichloromethane. The two dichloromethane layers were combined and dried over $MgSO_4$. The dichloromethane was removed with a rotoevaporator to yield 93 g (64%) of 2-[N,N'-di(2-hydroxyethyl)]thiopheneamide.

A one liter, three necked flask was equipped with overhead stirrer, nitrogen atmosphere and an addition funnel. The flask was charged with 85 g (64%) of 2-[N,N'-di(2-hydroxyethyl)]thiopheneamide (0.40 mol.), 80 g of triethylamine (0.80 mol.), 500 ml of tetrahydrofuran and 1 g of phenothiazine. Next, 72 g of acryloyl chloride (0.80 mol.) was slowly added to the reaction over 1.5 hour. The reaction was stirred at room temperature for 12 hours. The triethylamine hydrochloride salt was removed by filtration and the mother liquor evaporated with a rotoevaporator. The remaining liquid was dissolved in chloroform and washed with NaCl(aq.), $NH_4OH$ (10%), NaCl(aq.) and $MgSO_4$. The chloroform was removed with a rotoevaporator to yield 58 g (45%) of a light red liquid. The compound was confirmed by IR and $^{13}C$ NMR.

Example 15.

5-Acryloyloxymethyl-oxazolidin-2-one (OXA)

To a three liter flask equipped with a paddle stirrer, thermometer and addition funnel was added 91.5 g (1.0 mol.) of 3-amino-1,2-propanediol, followed by 2.2 moles of 12.5% aqueous NaOH. The solution was chilled with an ice bath to 0° C. as a solution of 100 g of phosgene in 400 ml of toluene was added over a 30 minute period. The solution was allowed to stir overnight, while coming to room temperature. The toluene layer was discarded and the aqueous layer was stripped on a rotoevaporator to a pasty liquid. Several hundred milliliters of ethanol were added. The paste was triturated and filtered. The ethanol solution was concentrated on a rotoevaporator to give 105 g (90%) of a nearly colorless oil, identified by $^{13}C$ NMR to be 5-hydroxymethyl-oxazolidin-2-one.

105 g (0.90 moles) of 5-hydroxymethyl-oxazolidin-2-one were placed into a one liter, three necked, round bottomed flask equipped with a paddle stirrer and thermometer. This was followed by 500 ml of tetrahydrofuran, 101 g (1.0 mol.) of triethylamine and 0.5 g of phenothiazine. Stirring was started as 90 g (1.0 mol.) of acryloyl chloride were added dropwise in such a way that the contents of the flask were maintained at 30° C. or less. When the addition was complete, the contents were stirred overnight at room temperature. The triethylamine hydrochloride was filtered and the solution was allowed to stand over $NaHCO_3$ and $Na_2SO_4$. The solution was filtered, transferred to a one liter, round bottomed flask and placed on a rotoevaporator. The solution was concentrated by purging with a stream of air while rotating the flask. The resulting liquid was confirmed by $^{13}C$ NMR to contain a mixture of the desired compound and unreacted starting material.

Example 16.

N-(Acryloyloxyethyl)hexahydrophthalimide (6HPIA)

A one liter three necked flask was equipped with a mechanical stirrer, condenser and Dean-Stark trap. The flask was charged with 61 g of ethanolamine (1.0 mol.), 300 milliliters toluene, and 151 g of hexahydrophthalic anhydride (1.0 mol.). The reaction was refluxed for 4 hours at which time one mole of water had been collected from the azeotrope. The reaction flask was cooled to room temperature (about 25° C.). Next, the flask was charged with 72 g acrylic acid (1.0 mol.), 16 g p-toluenesulfonic acid (0.08 mol.), and 2 g of p-methoxyphenol (0.01 mol.). The reaction was refluxed for 16 hours at which time one mole of water had been collected from the azeotrope. Next, the reaction flask was placed under vacuum (15 mmHg, 2 kPa) and heated to 120° C. to insure removal of the toluene. The remaining liquid was collected to yield 254 g of 6HPIA (94%). The structure was confirmed by IR and $^{13}C$ NMR.

Example 17.
N-Acryloylmorpholine (AMORPH)

A one liter three-necked flask, equipped with a mechanical stirrer, addition funnel, and a calcium chloride drying tube was charged with morpholine (60 ml =59.8 g=0.686 mol.), triethylamine (100 ml=72.6 g =0.717 mol.), p-methoxyphenol (3 g=0.024 mol.), and methyl ethyl ketone (300 ml). The addition funnel was charged with acryloyl chloride (60 ml=66.8 g=0.738 mol.) and methyl ethyl ketone (60 ml). The acid chloride solution was added dropwise over 45 minutes to the stirred reaction mixture, which was kept below 40° C. by a water/ice bath. After an additional thirty minutes of stirring, the triethylamine hydrochloride was removed by filtration, and the volatiles were removed by rotary evaporation, ultimately at ca 50° C. for one hour under water aspirator (ca. 20 mmHg) vacuum. The resulting brown liquid AMORPH (85 g; 88% yield) was collected, and its structure was confirmed by IR.

Examples 18–28
Use of Aromatic Acrylates as Reactive Diluents in Acrylamide Resins In Examples 18–28, acrylamidomethyl novolak (AMN), made in accordance with U.S. Pat. No. 5,236,472; acrylamidomethylated glycoluril (GUAM), made in accordance with U.S. Pat. No. 5,055,113; and acrylamidomethylated phenol (AMP), made in accordance with U.S. Pat. No. 4,903,440, were used in various resin formulations with the inventive reactive diluent compounds as detailed in Table 1. In each example, the resin/reactive diluent was coated onto glass microscope slides as explained above in the "Knoop Hardness Test", and the hardness tested after UV Cure and after UV cure plus thermal post cure.

TABLE 1

| Example No. | Parts Resin | Parts Reactive Diluent | UV cure (KNH) | UV cure + heat (KHN) |
| --- | --- | --- | --- | --- |
| 18 | 50 AMN | 50 CTA | 35 | 37 |
| 19 | 60 AMP | 40 DAMP | 33 | 35 |
| 20 | 60 AMP | 40 DAEP* | 34 | 34 |
| 21 | 60 AMP | 40 DAPP | 30 | 34 |
| 22 | 30 AMN, 30 GUAM | 40 DAP | 31 | 34 |
| 23 | 60 AMP | 40 SEA | 33 | 34 |
| 24 | 30 AMN, 30 GUAM | 40 PMMA | 26 | 33 |
| 25 | 60 AMP | 40 BA** | 26 | 25 |
| 26 | 60 AMP | 40 PEA** | 26 | 31 |
| 27 | 60 AMP | 40 BEA | 32 | 36 |
| 28 | 60 AMP | 40 PPEDA | 23 | 36 |

*"DAEP" is N,N'-di(acryloyloxyethyl)-N,N'-diethylphthalamide.
**Commercially available from Sartomer Company, Exton, PA wherein "BA" is benzylacrylate, and "PEA" is phenoyethyl acrylate.

Examples 29–35
Use of Imide Acrylate as Reactive Diluents in Acrylamide Resins Examples 29–35 were performed essentially the same as Examples 18–28 with the exception that different reactive diluents were employed as detailed in Table 2.

TABLE 2

| Example No. | Parts Resin | Parts Reactive Diluent | UV cure (KNH) | UV cure + heat (KHN) |
| --- | --- | --- | --- | --- |
| 29 | 60 AMP | 40 6HPIPA | 19 | 29 |
| 30 | 60 AMP | 40 4HPIDA | 30 | 35 |
| 31 | 60 AMP | 40 6HPIDA | 32 | 37 |
| 32 | 60 AMP | 40 MNIA | 35 | 38 |

TABLE 2-continued

| Example No. | Parts Resin | Parts Reactive Diluent | UV cure (KNH) | UV cure + heat (KHN) |
| --- | --- | --- | --- | --- |
| 33 | 60 AMP | 40 6HPIA | 36 | 38 |
| 34 | 60 AMP | 40 4HPIA | 37 | 38 |
| 35 | 60 AMP | 40 6HPIEEA | 17 | 31 |

Examples 36–58
Use of Heterocyclic Acrylates and Heterocyclic Acrylamides as Reactive Diluents in Acrylamide Resins Examples 36–58 were essentially the same as examples 18–35 except for the use of heterocyclic acrylate and heterocyclic acrylamide reactive diluents, as detailed in Table 3.

TABLE 3

| Example No. | Parts Resin | Parts Reactive Diluent | UV cure (KNH) | UV cure + heat (KHN) |
| --- | --- | --- | --- | --- |
| 36 | 60 AMP | 40 ThEA | 32 | 42 |
| 37 | 60 AMP | 40 FEA | 14 | 31 |
| 38 | 60 AMP | 40 OXDA | 35 | 40 |
| 39 | 60 AMP | 40 OXA | 25 | 38 |
| 40 | 60 AMP | 40 ThMAA | 4 | 18 |
| 41 | 60 AMP | 40 ThEAA | 16 | 35 |
| 42 | 60 AMP | 40 ThPAA | 18 | 30 |
| 43 | 60 AMP | 40 ThDEAA | 35 | 42 |
| 44 | 60 AMP | 40 FDEAA | 26 | 34 |
| 45 | 30 AMN, 30 GUAM | 40 GCA | 32 | 37 |
| 46 | 30 AMN, 30 GUAM | 40 KDM | 27 | 29 |
| 47 | 30 AMN, 30 GUAM | 40 KEM | 23 | 26 |
| 48 | 30 AMN, 30 GUAM | 40 KCP | 25 | 29 |
| 49 | 30 AMN, 30 GUAM | 40 KDME | 24 | 28 |
| 50 | 30 AMN, 30 GUAM | 40 KEEM | 23 | 27 |
| 51 | 60 AMP | 40 OXE | 26 | 34 |
| 52 | 60 AMP | 40 PYA | 34 | 38 |
| 53 | 60 AMP | 40 AMORPH | 32 | 44 |
| 54 | 60 AMP | 40 AMA | 18 | 24 |
| 55 | 60 AMP | 40 PEAA | 4 | 4 |
| 56 | 30 AMN, 30 GUAM | 40 RDUA | 13 | 36 |
| 57 | 60 AMP | 40 FAEA | 5 | 31 |

COATED ABRASIVE COMPARATIVE EXAMPLE A

For the following examples made using this procedure, the backing of each coated abrasive consisted of a J weight woven rayon jeans cloth which had a four over, one under, weave. To the surface of each backing which would hold the abrasive surface ("front") was applied a latex/phenolic resin pretreatment coating. The treated backings were heated until the pretreatment resin had cured to a tack-free state. Each backing made by this procedure was completely pretreated and was ready to receive a make coating.

The backing for this example was a J weight rayon backing that had been pretreated as described above. This backing was coated with Composition A consisting of a conventional calcium carbonate filled resole phenolic resin (84% by weight solids) to form a make coating. The wet coating weight was approximately 80 grams/meter$^2$ (gsm). Grade P120 aluminum oxide abrasive grains (average particle size about 130 micrometers) were electrostatically coated onto the make coating at a weight of approximately 209 gsm. The resulting abrasive article was precured for 30 minutes at 88° C. Composition B, a calcium carbonate filled phenolic resin diluted with HP and water, was applied over the abrasive grains and make coating at an average weight of approximately 100 gsm to form a size coating. The resulting construction was final cured for 10 hours at 100° C.

COATED ABRASIVE EXAMPLES 1-4

The procedure of Comparative Example A was followed except that make coating compositions 1-4 (See Table 4) were applied at a coating weight of 51 gsm followed by the application of 209 gsm of grade P120 (average particle size about 130 micrometers) aluminum oxide. These make coatings were UV precured using one 118 watt/cm lamp at 4.6 meters/min web speed. Size coating compositions 1-4 (See Table 1) diluted with isopropanol were applied over the abrasive grains and the make coating at an average dry weight of approximately 66 gsm. The size resin was cured by two 118 watt/cm lamps at 4.6 meters/min. for final cure plus an additional one hour at 120° C. The abrasive articles of Comparative Example A and Examples 1-4 were evaluated for performance using test procedures TP1, TP2, and TP3. Results are set forth in Table 2.

COATED ABRASIVE COMPARATIVE EXAMPLE B

A coated abrasive disc was prepared according to the following procedure. A 0.76 millimeter (mm) thick vulcanized fiber backing having a 2.2 centimeter (cm) diameter center hole was coated with Composition C consisting of a conventional calcium carbonate filled resole phenolic resin (83% by weight solids) to form a make coating. The wet coating weight was approximately 184 gsm. Grade 50 (average particle size about 400 micrometers) aluminum oxide abrasive grains were drop coated onto the make coating at a weight of approximately 552 gsm. The resulting abrasive article was precured for 150 minutes at 88° C. A size coating precursor consisting of 32% RP1, 50.2% CRY, 1.5% IO, and 1.6% HP and 14.4% water was applied over the abrasive grains and the make coating at an average weight of approximately 310 gsm to form a size coating. The resulting product was cured for 11-½ hours at 100° C. After this step, the coated abrasive discs were flexed and humidified at 45% Relative Humidity (RH) for one week prior to testing.

COATED ABRASIVE EXAMPLES 5-7

The procedure of Comparative Example B was followed except that make coating precursor compositions 5-7 (See Table 6) were applied at a dry coating weight of 153 gsm followed by the application of 552 gsm grade 50 (average particle size about 400 micrometers) aluminum oxide. These make coatings were UV precured using four passes at 6.1 meters/min. with a 118 watt/cm Fusion Systems D bulb. The same size coating as for Comparative Example B was applied followed by the same thermal size precure and a final cure of six hours at 121° C. Discs were humidified at 45% RH for one week prior to testing. Abrasive articles of Comparative Example B and Examples 5-7 were evaluated for performance using test procedures TP4 and TP5. The results are set forth in Table 7.

Data in Table 8 compare the hardness (KHN) of a standard resole phenolic, RP1, with the hardness of new compositions described herein comprising aminoplasts and reactive diluents, DAP and 6HPIA.

TABLE 4

| | BINDER RESIN COMPOSITIONS | | | | | |
|---|---|---|---|---|---|---|
| INGREDIENT | A | B | 1 | 2 | 3 | 4 |
| RP-1 | 53.2 | 50.6 | — | — | — | — |
| CACO | 43.7 | 40.6 | 50.0 | 50.0 | 50.0 | 50.0 |
| HP | 0.8 | 0.9 | — | — | — | — |
| TATHEIC | — | — | 25.0 | — | — | — |
| TMPTA | — | — | 25.0 | — | — | — |

TABLE 4-continued

| | BINDER RESIN COMPOSITIONS | | | | | |
|---|---|---|---|---|---|---|
| INGREDIENT | A | B | 1 | 2 | 3 | 4 |
| PH1 | — | — | 0.7 | 0.7 | 0.7 | 0.7 |
| GUAM | — | — | — | 20.0 | 10.0 | — |
| AMP | — | — | — | 5.0 | 15.0 | 21.7 |
| DAP | — | — | — | 10.0 | 10.0 | 6.5 |
| NPGDA | — | — | — | 15.0 | 15.0 | 6.5 |
| PETA | — | — | — | — | — | 8.7 |
| 6HPIA | — | — | — | — | — | 6.5 |
| water | 3.7 | 7.9 | — | — | — | — |

TABLE 5

PERFORMANCE OF ABRASIVE CONSTRUCTIONS

| COATED ABRASIVE | | | % PERFORMANCE | | |
|---|---|---|---|---|---|
| EXAMPLE NUMBER | MAKE FORMULA | SIZE FORMULA | TEST TP1 | TEST TP2 | TEST TP3 |
| COMPARATIVE A | A | B | 100 | 100 | 100 |
| 1 | 1 | 1 | 78 | 62 | 99 |
| 2 | 2 | 2 | 81 | 63 | 119 |
| 3 | 3 | 3 | 63 | 53 | 119 |
| 4 | 4 | 4 | 59 | 44 | 117 |

TABLE 6

| | BINDER RESIN COMPOSITIONS | | | |
|---|---|---|---|---|
| INGREDIENT | C | 5 | 6 | 7 |
| RP-1 | 59.0 | 27.5 | 27.5 | 27.5 |
| CACO | 38.2 | 50.0 | 50.0 | 50.0 |
| HP | 0.3 | 2.0 | — | — |
| PH1 | — | 0.7 | 0.7 | 0.7 |
| BAM | — | 20.5 | — | — |
| DAP | — | — | 22.5 | — |
| T₄EGDA | — | — | — | 22.5 |
| water | 2.5 | — | — | — |

TABLE 7

PERFORMANCE OF ABRASIVE CONSTRUCTIONS

| COATED | | % PERFORMANCE | |
|---|---|---|---|
| ABRASIVE EXAMPLE NO. | MAKE FORMULA | TEST TP4 | TEST TP5 |
| COMPARATIVE B | C | 100 | 100 |
| 5 | 5 | 93 | 87 |
| 6 | 6 | 94 | 88 |
| 7 | 7 | 86 | 83 |

The edge test (TP4) results, given in Table 7, illustrate equivalent performance with DAP, BAM, and the phenolic control. The T₄EGDA discs showed severe shelling and reduced cut. The slide action (TP5) results showed the phenolic control discs outperformed the DAP and BAM discs (total cut 88 and 87% of the control, respectively). The T4EDGA discs again performed the worst at 83% of the control and remarkably also showed some shelling on this low pressure test (4.5 kg. load). The results clearly demonstrate the superiority of the new reactive diluent, DAP, to the conventional diluent, T₄EGDA. In addition the results show that DAP performance is equivalent to BAM. DAP is a low viscosity (200 cps) liquid and may offer processing advantages to the solid BAM. The DAP blends exhibited a very fast UV cure, superior to T4EDGA, and were indistinguishable from BAM.

TABLE 8

KNOOP HARDNESS NUMBER
OF CURED BINDER COMPOSITIONS

| Cured Binder Composition | Type of Cure* | KHN After Cure |
|---|---|---|
| RP1 | T | 44 |
| 30% AMN/30% GUAM/ 40% DAP | UV | 31 |
|  | UV + heat | 34 |
| 60% AMP/40% 6HPIA | UV | 36 |
|  | UV + heat | 38 |

*Cure Conditions:
T = Thermal; 12 hours at 100° C.
UV = Four passes at 6.1 m/min. with a 118 watt/cm Fusion Systems "D" Bulb
Heat = 1.5 hours at 140° C.

COATED ABRASIVE COMPARATIVE EXAMPLE C

A coated abrasive disc was prepared according to the following procedure. A 0.81 millimeter (mm) thick fiberglass reinforced nylon backing 17.8 centimeters (cm) in diameter having a 2.2 cm diameter center hole was coated with Composition D consisting of a conventional calcium carbonate filled resole phenolic resin (81% by weight solids) to form a make coating. The backing was made in accordance with the teachings of the previously mentioned PCT application 9312912. The wet coating weight was approximately 131 gsm. Grade P80 (average particle size 250 micrometers) aluminum oxide abrasive grains were electrostatically coated onto the make coating at a weight of approximately 487 gsm. The resulting abrasive article was precured for 120 minutes at 88° C. A size coating precursor consisting of 31.7% RP1, 48.4% CRY, 1.5% IO, 3.7% HP and 14.7% water was applied over the abrasive grains and the make coating at an average weight of approximately 360 gsm to form a size coating. The resulting product was cured for 2 hours at 88° C., 10 hours at 100° C. and 12 hours at 125° C.

COATED ABRASIVE EXAMPLES 8–13

The procedure of Comparative Example C was followed except that make coating precursor compositions 8–13 (See Table 9) were applied at a dry coating weight of 127 gsm followed by the application of 491 gsm grade P80 (average particle size 150 micrometers) aluminum oxide. These make coatings were UV precured using 3 passes at 18.3 meters/min., 2 passes at 13.7 meters/min. and 1 pass at 9.1 meters/min. with a 118 watt/cm Fusion Systems D bulb. The same size coating as for Comparative Example C was applied followed by the same thermal size cure. Abrasive articles of Comparative Example C and Examples 8–13 were evaluated for performance using test procedure TP5. The results are set forth in Table 10.

TABLE 9

BINDER RESIN POSITIONS

| INGREDIENT | D | 5 | 6 | 7 | 8 | 9 | 10 |
|---|---|---|---|---|---|---|---|
| RP-1 | 73.0 | — | — | — | — | — | — |
| CACO | 46.0 | 46.0 | 46.0 | 46.0 | 46.0 | 46.0 | 46.0 |
| HP | 1.0 | — | — | — | — | — | — |
| Water | 4.0 | — | — | — | — | — | — |
| AMP | — | 18.4 | 18.4 | 18.4 | 22.1 | 22.1 | 22.1 |
| GUAM | — | 12.0 | 12.0 | 12.0 | 14.4 | 14.4 | 14.4 |
| DAP | — | 16.2 | 16.2 | 16.2 | 13.0 | 13.0 | 13.0 |

TABLE 9-continued

BINDER RESIN POSITIONS

| INGREDIENT | D | 5 | 6 | 7 | 8 | 9 | 10 |
|---|---|---|---|---|---|---|---|
| NPGDA | — | 10.8 | — | — | 8.6 | — | — |
| PYA | — | — | 10.8 | — | — | 8.6 | — |
| AMORPH | — | — | — | 10.8 | — | — | 8.6 |
| PH1 | — | 1.5 | 1.5 | 1.5 | 1.5 | 1.5 | 1.5 |

TABLE 10

PERFORMANCE OF ABRASIVE CONSTRUCTIONS

| Coated Abrasive Example No. | Make Formula | % Performance Test TP5 |
|---|---|---|
| Comparative C | D | 100.0 |
| 8 | 5 | 92.5 |
| 9 | 6 | 89.0 |
| 10 | 7 | 94.6 |
| 11 | 8 | 101.7 |
| 12 | 9 | 95.8 |
| 13 | 10 | 102.3 |

Dynamic Mechanical Analysis: Example 1 and Comparative Examples A and B

Dynamic mechanical analysis was performed on three compositions. The composition of Example 1 consisted of 50 parts acrylamidomethylated phenol (AMP), produced in accordance with U.S. Pat. No. 4,903,440, 50 parts N-(acryloyl)morpholine (AMORPH), and 1.5 part PH1, based on %100 solids. The composition of Comparative Example A consisted only of 100 parts AMP and 1.5 part PH1. The composition of Comparative Example B consisted of 50 parts AMP, 50 parts PEA and 1.5 part PH1.

Figure 5:
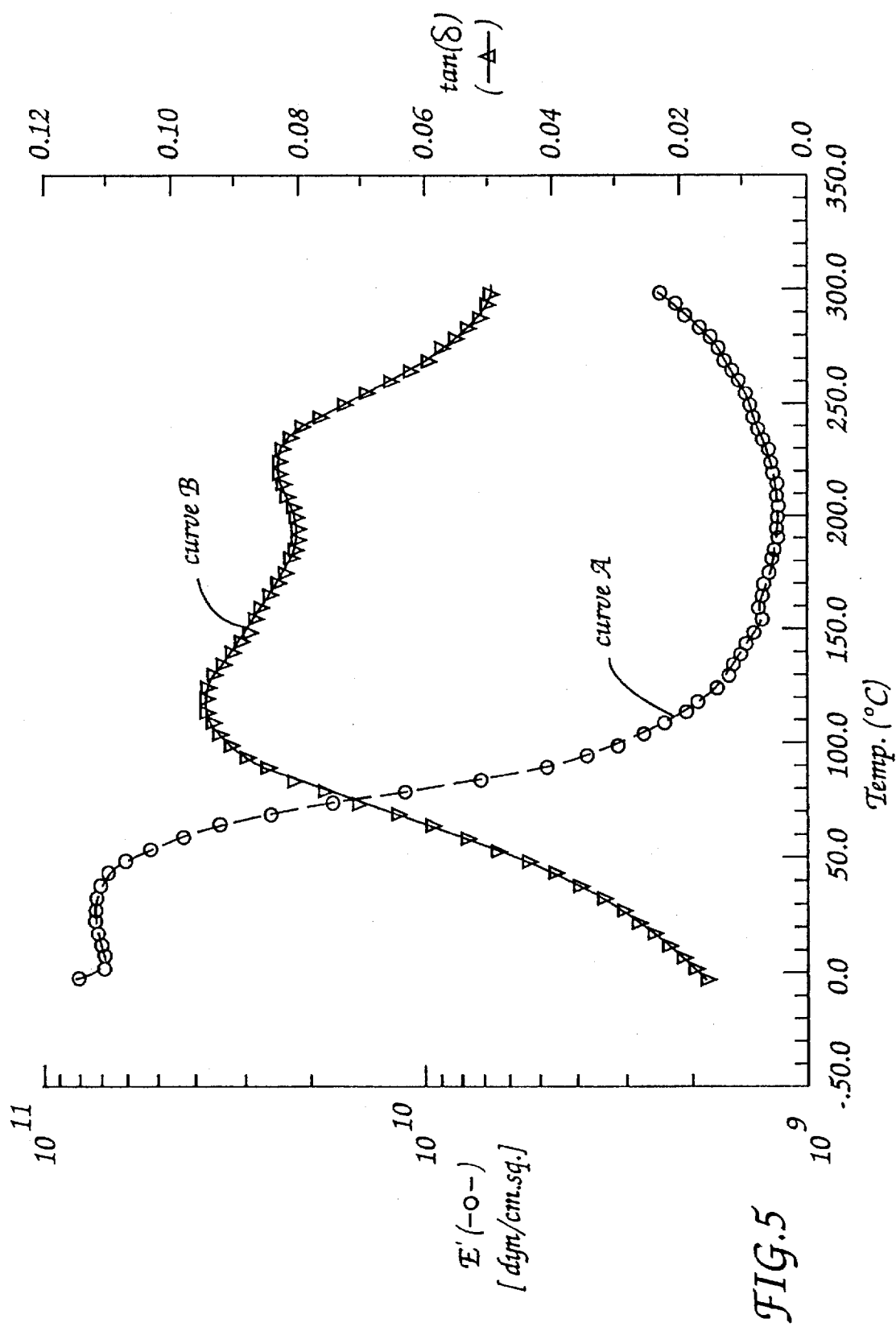
FIGS. 5–7 are graphical representations of dynamic mechanical analysis (DMA) of compositions, with FIG. 5 generated using only resin with no diluent, FIG. 6 generated using a composition of the invention, and FIG. 7 generated using a composition outside of the invention.
Figure 6:
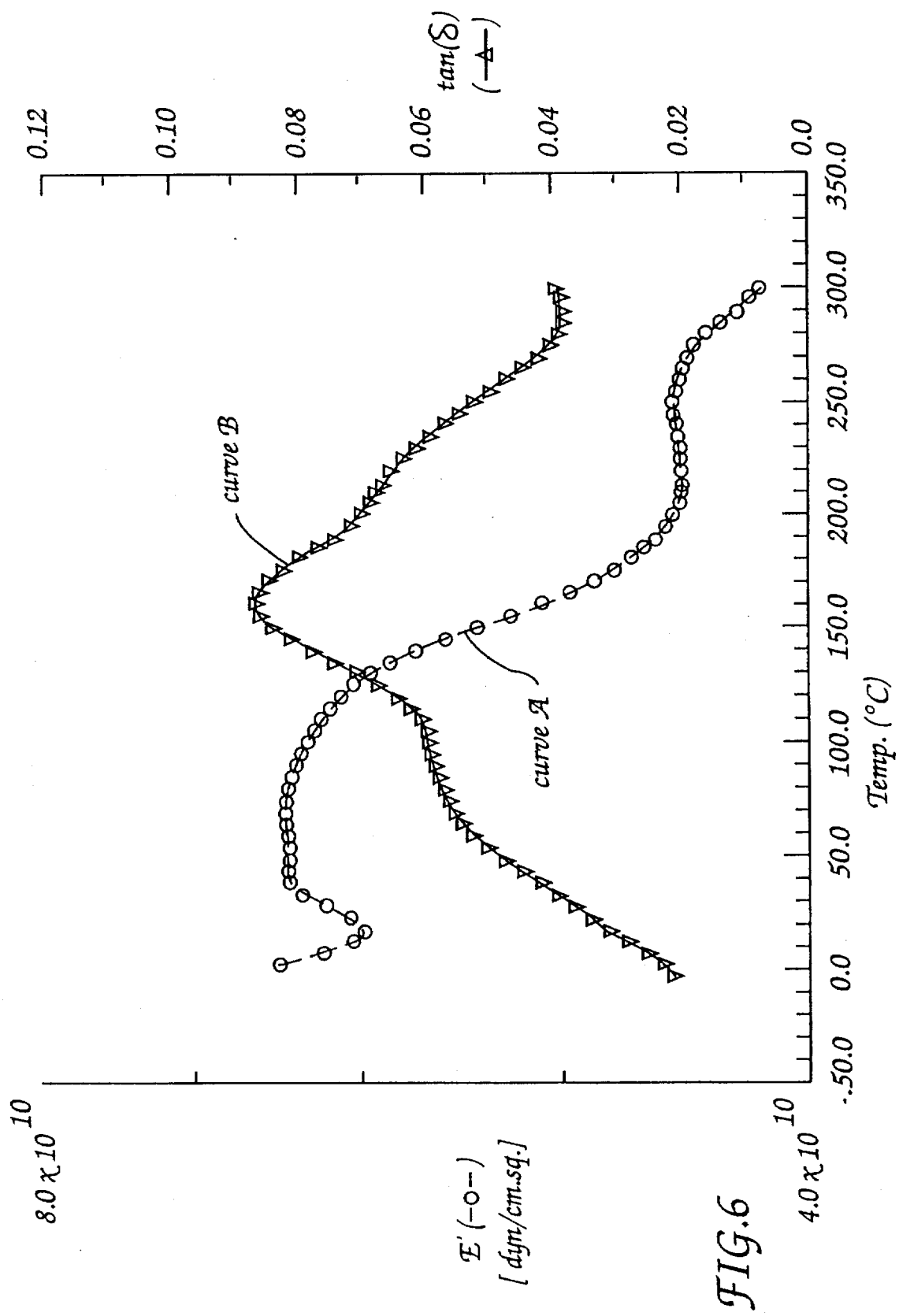
Figure 7:
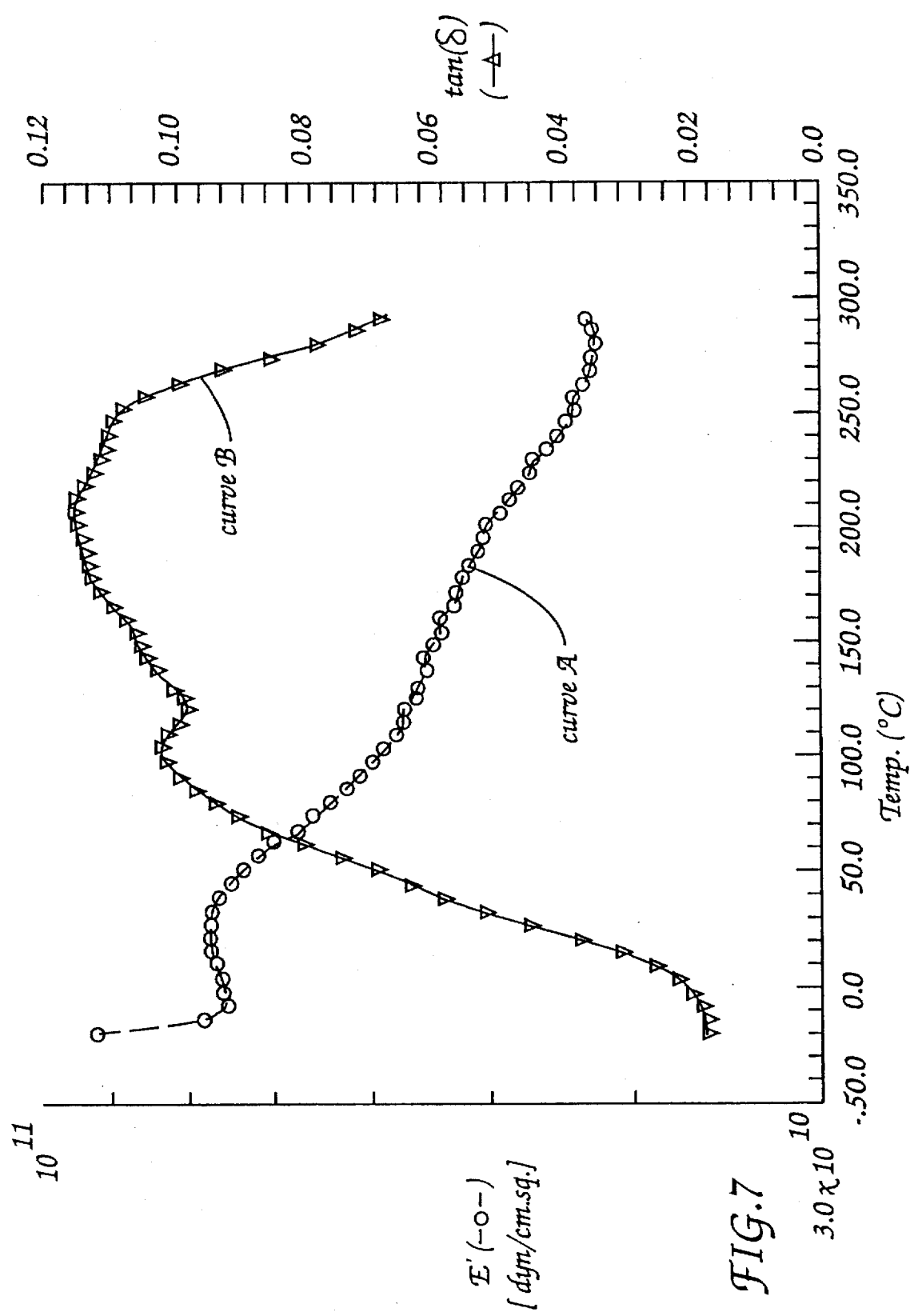

The results of the dynamic mechanical analysis are presented in Tables 11, 12, and 13 and in graphical form in FIGS. 5, 6, and 7 (Comparative Example A, Example 1, and Comparative Example B, respectively). Note from FIG. 5 the additional curing occuring above 190° C. for Comparative Example A as evidenced by the second hump in the tan δ curve (curve B) and the increase in the E' curve (curve A). For the composition within the invention (Example 1), FIG. 6 illustrates that the cured resin does not soften until temperatures above 120° C., whereas for Comparative Example A (FIG. 7) the tan δ curve (curve B) is too broad to define $T_g$. In FIG. 7 it will be noted that the composition exhibited better cure with the diluent with the pure resin (FIG. 6), and that the composition of Comparative Example A softened with increase in temperature as evidenced by the E' curve (curve A). In addition, the composition of Comparative Example B (FIG. 7) softened with temperature increase as evidenced by the increase in E' (curve A), characteristic of a broad molecular weight distribution.

TABLE 11

Notes: 100 parts AMP, 1.5 part PH1
sample size (mm): thickness = 0.30, width = 1.41,
length = 23.00

| Point | TEMP °C. | E' Dyne/cm$^2$ | tan δ |
|---|---|---|---|
| 1 | −2.8 | 8.084e+10 | 1.477e−02 |
| 2 | 1.7 | 6.917e+10 | 1.746e−02 |
| 3 | 7.5 | 6.942e+10 | 1.978e−02 |
| 4 | 12.5 | 7.084e+10 | 2.185e−02 |
| 5 | 17.6 | 7.236e+10 | 2.356e−02 |

TABLE 11-continued

Notes: 100 parts AMP, 1.5 part PH1
sample size (mm): thickness = 0.30, width = 1.41, length = 23.00

| Point | TEMP °C. | E' Dyne/cm$^2$ | tan δ |
|---|---|---|---|
| 6 | 22.7 | 7.354e+10 | 2.674e−02 |
| 7 | 27.7 | 7.362e+10 | 2.759e−02 |
| 8 | 32.8 | 7.282e+10 | 3.309e−02 |
| 9 | 38.0 | 7.124e+10 | 3.419e−02 |
| 10 | 43.2 | 6.757e+10 | 3.884e−02 |
| 11 | 48.5 | 6.103e+10 | 4.410e−02 |
| 12 | 53.5 | 5.263e+10 | 4.927e−02 |
| 13 | 58.7 | 4.316e+10 | 5.315e−02 |
| 14 | 64.5 | 3.467e+10 | 5.848e−02 |
| 15 | 68.8 | 2.558e+10 | 6.389e−02 |
| 16 | 74.0 | 1.754e+10 | 6.966e−02 |
| 17 | 79.0 | 1.129e+10 | 7.902e−02 |
| 18 | 84.2 | 7.165e+09 | 8.117e−02 |
| 19 | 89.8 | 4.789e+09 | 8.449e−02 |
| 20 | 94.6 | 3.750e+09 | 8.971e−02 |
| 21 | 99.4 | 3.102e+09 | 9.082e−02 |
| 22 | 104.4 | 2.655e+09 | 9.378e−02 |
| 23 | 109.3 | 2.334e+09 | 9.406e−02 |
| 24 | 114.5 | 2.060e+09 | 9.669e−02 |
| 25 | 118.2 | 1.930e+09 | 8.798e−02 |
| 26 | 124.6 | 1.720e+09 | 1.012e−01 |
| 27 | 130.0 | 1.587e+09 | 9.493e−02 |
| 28 | 134.6 | 1.550e+09 | 8.954e−02 |
| 29 | 139.8 | 1.472e+09 | 9.119e−02 |
| 30 | 144.7 | 1.429e+09 | 8.726e−02 |
| 31 | 148.9 | 1.365e+09 | 9.132e−02 |
| 32 | 155.2 | 1.299e+09 | 8.621e−02 |
| 33 | 159.9 | 1.328e+09 | 8.421e−02 |
| 34 | 165.2 | 1.299e+09 | 8.560e−02 |
| 35 | 170.1 | 1.289e+09 | 8.498e−02 |
| 36 | 175.0 | 1.250e+09 | 8.361e−02 |
| 37 | 181.6 | 1.227e+09 | 7.632e−02 |
| 38 | 185.1 | 1.210e+09 | 8.290e−02 |
| 39 | 190.4 | 1.187e+09 | 8.332e−02 |
| 40 | 194.7 | 1.197e+09 | 7.679e−02 |
| 41 | 200.1 | 1.185e+09 | 7.988e−02 |
| 42 | 205.1 | 1.172e+09 | 8.356e−02 |
| 43 | 209.7 | 1.190e+09 | 8.093e−02 |
| 44 | 215.2 | 1.191e+09 | 8.277e−02 |
| 45 | 219.8 | 1.219e+09 | 8.431e−02 |
| 46 | 224.8 | 1.231e+09 | 8.375e−02 |
| 47 | 230.8 | 1.255e+09 | 8.351e−02 |
| 48 | 235.0 | 1.299e+09 | 8.075e−02 |
| 49 | 240.3 | 1.337e+09 | 8.154e−02 |
| 50 | 244.7 | 1.371e+09 | 7.824e−02 |
| 51 | 250.0 | 1.395e+09 | 7.166e−02 |
| 52 | 255.1 | 1.434e+09 | 6.919e−02 |
| 53 | 260.6 | 1.493e+09 | 6.522e−02 |
| 54 | 265.4 | 1.557e+09 | 6.485e−02 |
| 55 | 269.7 | 1.624e+09 | 5.670e−02 |
| 56 | 275.2 | 1.687e+09 | 5.737e−02 |
| 57 | 279.7 | 1.770e+09 | 5.670e−02 |
| 58 | 283.7 | 1.900e+09 | 5.347e−02 |
| 59 | 289.1 | 2.072e+09 | 4.942e−02 |
| 60 | 294.5 | 2.194e+09 | 5.199e−02 |
| 61 | 298.8 | 2.401e+09 | 4.879e−02 |

TABLE 12

Notes:
50 parts AMP, 50 parts AMORPH, 1.5 part PH1
sample size (mm): thickness = 0.21, width = 1.33, length = 23.00

| Point | TEMP °C. | E' Dyne/cm$^2$ | tan δ |
|---|---|---|---|
| 1 | −3.1 | 9.443e+10 | 2.106e−02 |
| 2 | 2.3 | 6.758e+10 | 2.014e−02 |
| 3 | 7.1 | 6.022e+10 | 2.625e−02 |
| 4 | 12.5 | 5.845e+10 | 3.010e−02 |
| 5 | 16.7 | 5.885e+10 | 3.150e−02 |
| 6 | 22.6 | 6.073e+10 | 3.395e−02 |
| 7 | 27.7 | 6.254e+10 | 3.713e−02 |
| 8 | 32.7 | 6.396e+10 | 3.853e−02 |
| 9 | 38.1 | 6.447e+10 | 4.300e−02 |
| 10 | 43.0 | 6.447e+10 | 4.489e−02 |
| 11 | 47.9 | 6.367e+10 | 4.740e−02 |
| 12 | 53.6 | 6.418e+10 | 5.040e−02 |
| 13 | 58.4 | 6.422e+10 | 5.358e−02 |
| 14 | 63.9 | 6.429e+10 | 5.511e−02 |
| 15 | 68.6 | 6.443e+10 | 5.609e−02 |
| 16 | 73.9 | 6.467e+10 | 5.707e−02 |
| 17 | 79.2 | 6.412e+10 | 5.646e−02 |
| 18 | 84.1 | 6.392e+10 | 5.805e−02 |
| 19 | 89.5 | 6.389e+10 | 5.964e−02 |
| 20 | 94.2 | 6.346e+10 | 6.068e−02 |
| 21 | 99.6 | 6.301e+10 | 5.811e−02 |
| 22 | 104.6 | 6.265e+10 | 6.062e−02 |
| 23 | 110.0 | 6.214e+10 | 6.136e−02 |
| 24 | 114.5 | 6.179e+10 | 6.080e−02 |
| 25 | 119.4 | 6.162e+10 | 6.448e−02 |
| 26 | 124.9 | 6.040e+10 | 6.798e−02 |
| 27 | 129.4 | 5.932e+10 | 7.031e−02 |
| 28 | 134.3 | 5.871e+10 | 7.607e−02 |
| 29 | 139.2 | 5.744e+10 | 7.798e−02 |
| 30 | 144.9 | 5.567e+10 | 8.074e−02 |
| 31 | 149.6 | 5.400e+10 | 8.547e−02 |
| 32 | 155.0 | 5.231e+10 | 8.741e−02 |
| 33 | 160.5 | 5.071e+10 | 8.884e−02 |
| 34 | 165.3 | 4.962e+10 | 8.683e−02 |
| 35 | 170.5 | 4.841e+10 | 8.520e−02 |
| 36 | 174.9 | 4.780e+10 | 8.262e−02 |
| 37 | 180.6 | 4.687e+10 | 8.046e−02 |
| 38 | 185.0 | 4.636e+10 | 7.829e−02 |
| 39 | 188.7 | 4.570e+10 | 7.454e−02 |
| 40 | 194.7 | 4.589e+10 | 7.132e−02 |
| 41 | 200.1 | 4.524e+10 | 6.867e−02 |
| 42 | 205.2 | 4.476e+10 | 7.030e−02 |
| 43 | 209.8 | 4.459e+10 | 6.779e−02 |
| 44 | 213.1 | 4.492e+10 | 6.849e−02 |
| 45 | 219.6 | 4.513e+10 | 6.527e−02 |
| 46 | 225.2 | 4.503e+10 | 6.322e−02 |
| 47 | 229.8 | 4.484e+10 | 6.236e−02 |
| 48 | 234.7 | 4.492e+10 | 6.105e−02 |
| 49 | 240.8 | 4.498e+10 | 5.566e−02 |
| 50 | 244.7 | 4.535e+10 | 5.480e−02 |
| 51 | 250.3 | 4.533e+10 | 5.327e−02 |
| 52 | 254.8 | 4.536e+10 | 4.856e−02 |
| 53 | 260.2 | 4.342e+10 | 7.874e−02 |
| 54 | 265.1 | 4.462e+10 | 4.502e−02 |
| 55 | 269.0 | 4.423e+10 | 4.238e−02 |
| 56 | 274.7 | 4.496e+10 | 3.957e−02 |
| 57 | 279.6 | 4.467e+10 | 3.969e−02 |
| 58 | 284.9 | 4.249e+10 | 9.458e−02 |
| 59 | 289.3 | 4.291e+10 | 3.767e−02 |
| 60 | 295.6 | 4.167e+10 | 5.315e−02 |
| 61 | 299.2 | 4.199e+10 | 4.031e−02 |

TABLE 13

Notes:
50 parts AMP, 50 parts PEA, 1.5 part PH1
Sample size (mm): thickness = 0.16, width = 1.26, length = 23.00

| Point | TEMP °C. | E' Dyne/cm$^2$ | tan δ |
|---|---|---|---|
| 1 | −22.8 | 9.194e+10 | 1.557e−02 |
| 2 | −17.7 | 7.815e+10 | 1.398e−02 |
| 3 | −12.4 | 7.532e+10 | 1.526e−02 |
| 4 | −7.3 | 7.568e+10 | 1.611e−02 |
| 5 | −1.8 | 7.605e+10 | 1.630e−02 |
| 6 | 3.3 | 7.665e+10 | 1.691e−02 |
| 7 | 8.3 | 7.736e+10 | 1.843e−02 |
| 8 | 13.0 | 7.744e+10 | 2.069e−02 |
| 9 | 18.3 | 7.724e+10 | 2.271e−02 |
| 10 | 23.0 | 7.719e+10 | 2.643e−02 |
| 11 | 28.1 | 7.628e+10 | 2.582e−02 |
| 12 | 33.4 | 7.492e+10 | 3.028e−02 |
| 13 | 38.8 | 7.350e+10 | 2.869e−02 |
| 14 | 43.6 | 7.196e+10 | 3.114e−02 |
| 15 | 48.8 | 7.009e+10 | 3.370e−02 |
| 16 | 52.9 | 6.743e+10 | 3.609e−02 |
| 17 | 59.0 | 6.593e+10 | 3.612e−02 |
| 18 | 63.9 | 6.421e+10 | 3.798e−02 |
| 19 | 69.4 | 6.260e+10 | 3.763e−02 |
| 20 | 74.1 | 6.135e+10 | 3.920e−02 |
| 21 | 79.8 | 6.025e+10 | 4.031e−02 |
| 22 | 85.0 | 5.899e+10 | 3.890e−02 |
| 23 | 89.6 | 5.783e+10 | 4.116e−02 |
| 24 | 94.5 | 5.732e+10 | 3.914e−02 |
| 25 | 100.0 | 5.707e+10 | 3.725e−02 |
| 26 | 104.7 | 5.619e+10 | 3.762e−02 |
| 27 | 107.9 | 5.604e+10 | 3.994e−02 |
| 28 | 115.1 | 5.524e+10 | 4.087e−02 |
| 29 | 120.0 | 5.529e+10 | 3.954e−02 |
| 30 | 124.8 | 5.460e+10 | 4.122e−02 |
| 31 | 129.9 | 5.394e+10 | 4.153e−02 |
| 32 | 134.9 | 5.404e+10 | 4.002e−02 |
| 33 | 139.6 | 5.285e+10 | 4.189e−02 |
| 34 | 144.9 | 5.275e+10 | 4.254e−02 |
| 35 | 150.3 | 5.223e+10 | 4.455e−02 |
| 36 | 155.0 | 5.165e+10 | 4.293e−02 |
| 37 | 160.1 | 5.095e+10 | 4.226e−02 |
| 38 | 165.6 | 5.045e+10 | 4.188e−02 |
| 39 | 170.5 | 5.028e+10 | 4.481e−02 |
| 40 | 175.5 | 4.919e+10 | 4.532e−02 |
| 41 | 180.6 | 4.833e+10 | 4.187e−02 |
| 42 | 185.2 | 4.782e+10 | 4.372e−02 |
| 43 | 190.3 | 4.689e+10 | 4.196e−02 |
| 44 | 196.1 | 4.664e+10 | 4.280e−02 |
| 45 | 199.7 | 4.572e+10 | 4.385e−02 |
| 46 | 205.2 | 4.494e+10 | 3.907e−02 |
| 47 | 210.2 | 4.439e+10 | 4.434e−02 |
| 48 | 214.8 | 4.371e+10 | 3.994e−02 |
| 49 | 219.6 | 4.387e+10 | 4.240e−02 |
| 50 | 224.4 | 4.318e+10 | 3.877e−02 |
| 51 | 230.1 | 4.269e+10 | 3.802e−02 |
| 52 | 235.0 | 4.267e+10 | 3.310e−02 |
| 53 | 239.7 | 4.239e+10 | 3.291e−02 |
| 54 | 245.8 | 4.260e+10 | 3.187e−02 |
| 55 | 249.2 | 4.303e+10 | 2.845e−02 |

This work provided evidence that abrasive articles made with coatable, radiation curable binder precursor compositions using the reactive diluents described herein can perform as well as or better than previously known abrasive articles. Although the above examples are intended to be representative of the invention, they are not intended to limit the scope of appendant claims.

What is claimed is:

1. A coated abrasive article comprising a backing upon which an abrasive coating comprising a plurality of abrasive grains and a binder is attached, at least a portion of said binder formed from a coatable, addition polymerizable binder precursor composition comprising an organic compound selected from the group consisting of:

(a) compounds selected from the group consisting of compounds within general formula (I):

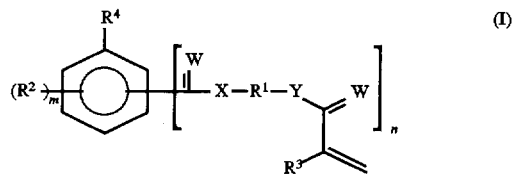

wherein:

R$^1$ is an organic radical devoid of reactive groups other than optional ethylenically-unsaturated groups and is selected from the group consisting of radicals having from 1 to 12 carbon atoms;

R$^2$ is selected from the group consisting of: i) organic radicals devoid of reactive groups other than optional ethylenically-unsaturated groups and selected from the group consisting of organic radicals having from 1 to 12 carbon atoms, and ii) moieties which do not substantially terminate polymerization of ethylenically-unsaturated groups;

R$^3$ is selected from the group consisting of —H and organic radicals devoid of reactive groups other than optional ethylenically-unsaturated groups and selected from the group consisting of organic radicals having from 1 to 12 carbon atoms;

R$^4$ is selected from the group consisting of
—H, —OH, —O—C(=O)—C(R$^3$)=CH$_2$, and —NR$^3$—C(=O)—C(R$^3$)=CH$_2$;

W, X and Y are independently selected from the group consisting of O, S, NR$^3$;

m is an integer ranging from 0 to 2, with the proviso that when m=2, R$^2$=adjacent substitutions which together form fused organic ring structures; and n is either 1 or 2;

(b) aromatic compounds selected from the group consisting of compounds within general formula (II):

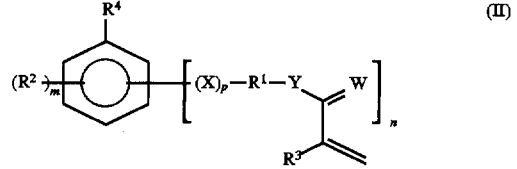

wherein:

R$^1$, R$^2$, R$^3$, R$^4$, W, X, Y, m and n are as defined for general formula (I) and p is 0 or 1, with the proviso that when R$^1$ is —CH$_2$CH$_2$—, R$^4$ is H, and m is 0, when X, Y, and W cannot all be O, and with the proviso that when p is 0 and R$^1$ is —CH$_2$—, Y cannot be NR$_3$ or O;

(c) N-substituted succinimide derivatives selected from the group consisting of compounds within general formula (III):

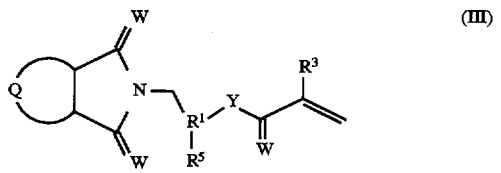

wherein:

R$^1$, R$^3$, W and Y are as defined for general formula (I);

$R^5$ is selected from the group consisting of —H, —(R$^1$)$_t$ —Y—C(=W)—CR$_3$=CH$_2$, and C$_1$-C$_{12}$ (inclusive) organic radicals;

Q is selected from the group consisting of cycloaliphatic residues, bicycloaliphatic residues, and aromatic residues, wherein the residues may have optional ring substituents which do not substantially interfere with free radical polymerization of ethylenically unsaturated groups; and t is 0 or 1;

(d) heterocyclic compounds selected from the group consisting of compounds within general formula (IV):

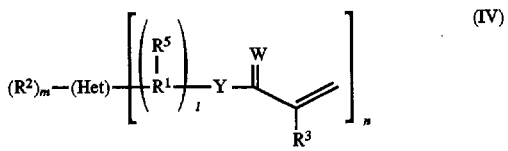

wherein:

R$^1$, R$^2$, R$^3$, W, Y, m, and n have the meaning set forth for general formula (I);

R$^5$ is selected from the group consisting of —H, —(R$^1$)$_t$ —Y—C(=W)—CR$_3$=CH$_2$, and C$_1$-C$_{12}$ (inclusive) organic radicals;

(Het) is a cyclic organic radical having at least one ring heteroatom;

l is 0 or 1; and t is 0 or 1; and (e) heterocyclic compounds selected from the group consisting of compounds within general formula (V):

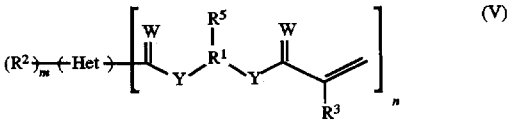

wherein:

R$^1$, R$^2$, R$^3$, R$^5$, W, Y, m, and n have the meanings set forth in general formula (IV);

and mixtures thereof.

2. A coated abrasive article in accordance with claim 1 comprising an additional polymerizable resin.

3. A coated abrasive article in accordance with claim 2 wherein the addition polymerizable resin is free radically polymerizable.

4. A coated abrasive article in accordance with claim 3 wherein the addition polymerizable resin comprises an aminoplast resin having α,β-unsaturated carbonyl groups.

5. A coated abrasive article comprising a backing, a make coating over at least one major surface of the backing, a plurality of abrasive grains adhered to the backing by the make coating, and a size coating over the abrasive grains, wherein at least one of the make or size coating is formed from the coatable, addition polymerizable binder precursor composition of claim 1.

6. A coated abrasive article comprising a backing, a make coating over at least one major surface of the backing, a plurality of coating over the abrasive grains, wherein at least one of the make or size abrasive grains adhered to the backing by the make coating, and a size coating is formed from the coatable, addition polymerizable binder precursor composition of claim 2.

7. A coated abrasive article in accordance with claim 6 wherein the addition polymerizable resin comprises an aminoplast resin having α,β-unsaturated carbonyl groups.

8. A coated abrasive article comprising a backing, a make coating over at least one major surface of the backing, a plurality of abrasive particles adhered to the backing by the make coating, and a size coating over the abrasive particles, wherein said backing has at least one of a saturant coating, a presize coating, or a backsize coating, wherein at least one of said saturant coating, said presized coating, or said backsize coating is formed from the coatable, addition polymerizable binder precursor composition of claim 1.

9. A coated abrasive article comprising a backing, a make coating over at least one major surface of the backing, a layer of abrasive particles adhered to the backing by the make coating, and a size coating over the abrasive particles, wherein said backing has at least one of a saturant coating, a presized coating, or a backsize coating, wherein at least one of said saturant coating, said presized coating, or said backsize coating is formed from the coatable, addition polymerizable binder precursor composition of claim 2.

10. A coated abrasive article in accordance with claim 9 wherein the addition polymerizable resin comprises an aminoplast resin having α,β-unsaturated carbonyl groups.

11. A method of making a coated abrasive article, said method comprising the steps of:

(a) coating at least one major surface of a backing with a coatable, addition polymerizable binder precursor composition comprising a compound and abrasive particles to provide a coated backing; and (b) subjecting the coated backing to conditions sufficient to cure the composition, wherein the compound is as defined in claim 1.

12. A method in accordance with claim 11 wherein the composition includes an addition polymerizable resin.

13. A method in accordance with claim 12 wherein the addition polymerizable resin comprises an aminoplast resin having α,β-unsaturated carbonyl groups.

14. A method of making a coated abrasive article comprising the steps of:

(a) applying a first coatable, addition polymerizable binder precursor composition to at least one major surface of a backing to form a make coating precursor, the coatable addition polymerizable binder precursor composition comprising a compound as defined in claim 1;

(b) applying abrasive particles to the make coating precursor of step (a) to form a wet abrasive coating;

(c) subjecting the wet abrasive coating to conditions sufficient to at least partially solidify the make coating precursor and form a first intermediate structure;

(d) applying a second coatable, addition polymerizable binder precursor composition optionally including a compound as defined in claim 1 to the first intermediate structure to form a second intermediate structure having a size coating; and (e) subjecting the second intermediate structure to conditions sufficient to cure the first and second coatable, addition polymerizable binder precursor compositions.

15. A method in accordance with claim 14 wherein either one or both of the first and second addition polymerizable binder precursor compositions comprises an aminoplast resin having α,β-unsaturated carbonyl groups.

* * * * *

UNITED STATES PATENT AND TRADEMARK OFFICE
CERTIFICATE OF CORRECTION

PATENT NO.: 5,667,842

DATED: September 16, 1997

INVENTOR(S): Eric G. Larson, Ernest L. Thurber, Alan R. Kirk, Gregg D. Dahlke, Elizabeth C. Edblom, Don H. Kincaid It is certified that error appears in the above-identified patent and that said Letters Patent is hereby corrected as shown below:

| | |
|---|---|
| Col. 3, line 51 | "$NR_3$" should read --$NR^3$-- |
| Col. 9, line 29 | "$NR_3$" should read --$NR^3$-- |
| Col. 9, line 63 | New paragraph starting with "$R^7$" |
| Col. 10, line 65 | After "--$C_xH_{2x+1}$" insert --; and-- |
| Col. 11, general formula (X) |  should read |
| Col. 11, line 47 | Delete "and" |
| Col. 12, line 7 | New paragraph starting with "t is 0" |
| Col. 13, line 60 | New paragraph starting with "Specifically" |
| Col. 15, line 48 | "pendantlacrylate" should read --pendant acrylate-- |
| Col. 16, line 57 | "9" should read --column 9-- |
| Col. 18, line 51 | "Ashland Chemical" should read --Ashland Chemical Co.-- |
| Col. 28, line 9 | "N-[2,3-Di(acryloyloxy)propyl)hexahydrophthalimide" should read --N-[2,3-Di(acryloyloxy)propyl]]hexahydrophthalimide--. |
| Col. 28, line 21 | Before "(OXDA)" insert --4,4-Di(acryloyloxymethyl)-2-oxazolidinone-- |
| Col. 31, line 9 | "N-(2,3-Di(acryloyloxy)propyl)hexahydrophthalimlde" should read --N-(2,3-Di(acryloyloxy)propyl)hexahydrophthalimide-- |

UNITED STATES PATENT AND TRADEMARK OFFICE
CERTIFICATE OF CORRECTION

PATENT NO.: 5,667,842

DATED: September 16, 1997

INVENTOR(S): Eric G. Larson, Ernest L. Thurber, Alan R. Kirk, Gregg D. Dahlke, Elizabeth C. Edblom, Don H. Kincaid It is certified that error appears in the above-identified patent and that said Letters Patent is hereby corrected as shown below:

| | |
|---|---|
| Col. 32, line 28 | After "added" insert --75 g-- |
| Col. 33, line 7 | "77 g" should read --75 g-- |
| Col. 38, Table 7 | "COATED ABRASIVE EXAMPLE NO." should read --5 COATED ABRASIVE EXAMPLE NO.-- |
| Col. 38, line 62 | "T4EDGA" should read --$T_4$EGDA-- |
| Col. 39, line 3 | "T4EDGA" should read --$T_4$EGDA-- |
| Col. 44, line 40 | "formula III)" should read --formula (II)-- |
| Col. 44, line 54 | "$NR_3$" should read --$NR^3$-- |
| Col. 45, lines 58-60 | "coating over the abrasive grains, wherein at least one of the make or size abrasive grains adhered to the backing by the make coating, and a size" should read --abrasive grains adhered to the backing by the make coating, and a size coating over the abrasive grains, wherein at least one of the make or size-- |

Signed and Sealed this

Fifteenth Day of December, 1998

Attest:

Attesting Officer

BRUCE LEHMAN

Commissioner of Patents and Trademarks